US011142848B2

(12) United States Patent
Glenn, Jr. et al.

(10) Patent No.: US 11,142,848 B2
(45) Date of Patent: *Oct. 12, 2021

(54) DISSOLVABLE FIBROUS WEB STRUCTURE ARTICLE COMPRISING ACTIVE AGENTS

(71) Applicant: The Procter & Gamble Company, Cincinnati, OH (US)

(72) Inventors: Robert Wayne Glenn, Jr., Liberty Township, OH (US); Rajeev Chhabra, Mason, OH (US); William Maxwell Allen, Jr., Liberty Township, OH (US); Jonathan Paul Brennan, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 488 days.

This patent is subject to a terminal disclaimer.

(21) Appl. No.: 15/978,503

(22) Filed: May 14, 2018

(65) Prior Publication Data

US 2018/0258555 A1    Sep. 13, 2018

Related U.S. Application Data

(60) Continuation of application No. 15/374,486, filed on Dec. 9, 2016, now abandoned, which is a continuation
(Continued)

(51) Int. Cl.
*D01D 5/42* (2006.01)
*A61Q 5/02* (2006.01)
(Continued)

(52) U.S. Cl.
CPC ........... *D01D 5/423* (2013.01); *A61K 8/0204* (2013.01); *A61K 8/0208* (2013.01); *A61K 8/345* (2013.01);
(Continued)

(58) Field of Classification Search
None
See application file for complete search history.

(56) References Cited

U.S. PATENT DOCUMENTS

| 2,356,168 A | 8/1944 | Mabley |
| 2,396,278 A | 3/1946 | Lind |

(Continued)

FOREIGN PATENT DOCUMENTS

| CN | 1138091 | 12/1996 |
| CN | 1219388 | 6/1999 |

(Continued)

OTHER PUBLICATIONS

International Search Report for PCT/IB2009/050388 dated Jul. 15, 2009.
(Continued)

*Primary Examiner* — Monica A Huson
(74) *Attorney, Agent, or Firm* — Parker D. McCrary

(57) ABSTRACT

The personal care compositions of the present invention are in the form of an Article comprising a dissolvable fibrous web structure. The fibers of the dissolvable fibrous web structure comprise a surfactant; a water soluble polymeric structurant; and a plasticizer. Additionally the ratio of the water soluble water soluble polymeric structurant to the active agent in the fiber is 3.5 or less.

28 Claims, 6 Drawing Sheets

Related U.S. Application Data of application No. 15/170,125, filed on Jun. 1, 2016, now Pat. No. 9,545,364, which is a division of application No. 14/334,862, filed on Jul. 18, 2014, now abandoned, which is a division of application No. 13/173,639, filed on Jun. 30, 2011, now abandoned.

(60) Provisional application No. 61/360,982, filed on Jul. 2, 2010.

(51) Int. Cl.

| | | |
|---|---|---|
| *A61Q 19/10* | (2006.01) | |
| *A61K 8/34* | (2006.01) | |
| *A61K 8/81* | (2006.01) | |
| *A61K 8/49* | (2006.01) | |
| *A61K 8/46* | (2006.01) | |
| *A61K 8/73* | (2006.01) | |
| *A61K 8/362* | (2006.01) | |
| *A61K 8/86* | (2006.01) | |
| *A61K 8/02* | (2006.01) | |
| *D01D 1/02* | (2006.01) | |
| *D01D 5/04* | (2006.01) | |
| *D01F 6/50* | (2006.01) | |
| *A61Q 19/00* | (2006.01) | |
| *D01D 5/253* | (2006.01) | |

(52) U.S. Cl.
CPC .............. *A61K 8/362* (2013.01); *A61K 8/463* (2013.01); *A61K 8/4946* (2013.01); *A61K 8/731* (2013.01); *A61K 8/8129* (2013.01); *A61K 8/86* (2013.01); *A61Q 5/02* (2013.01); *A61Q 19/00* (2013.01); *A61Q 19/10* (2013.01); *D01D 1/02* (2013.01); *D01D 5/04* (2013.01); *D01F 6/50* (2013.01); *A61K 2800/80* (2013.01); *D01D 5/253* (2013.01)

(56) References Cited

U.S. PATENT DOCUMENTS

| | | |
|---|---|---|
| 2,438,091 A | 3/1948 | Lynch |
| 2,486,921 A | 11/1949 | Byerly |
| 2,486,922 A | 11/1949 | Strain |
| 2,528,378 A | 10/1950 | Mannheimer |
| 2,658,072 A | 11/1953 | Kosmin |
| 2,694,668 A | 11/1954 | Fricke |
| 2,809,971 A | 10/1957 | Bernstein |
| 3,152,046 A | 10/1964 | Ales |
| 3,236,733 A | 2/1966 | Karsten |
| 3,321,425 A | 5/1967 | Blau et al. |
| 3,332,880 A | 7/1967 | Kessler |
| 3,426,440 A | 2/1969 | Shen |
| 3,489,688 A | 1/1970 | Pospischil |
| 3,653,383 A | 4/1972 | Wise |
| 3,695,989 A | 10/1972 | Albert |
| 3,753,196 A | 8/1973 | Kurtz et al. |
| 3,761,418 A | 9/1973 | Parran |
| 3,929,678 A | 12/1975 | Laughlin et al. |
| 3,957,921 A | 5/1976 | Iwahashi et al. |
| 4,020,156 A | 4/1977 | Murray et al. |
| 4,051,081 A | 9/1977 | Jabs et al. |
| 4,089,945 A | 5/1978 | Brinkman et al. |
| 4,149,551 A | 4/1979 | Benjamin et al. |
| 4,196,190 A | 4/1980 | Gehman et al. |
| 4,197,865 A | 4/1980 | Jacquet et al. |
| 4,206,196 A | 6/1980 | Davis |
| 4,217,914 A | 8/1980 | Jacquet et al. |
| 4,272,511 A | 6/1981 | Papantoniou et al. |
| 4,323,683 A | 4/1982 | Bolich, Jr. et al. |
| 4,345,080 A | 8/1982 | Bolich, Jr. |
| 4,379,753 A | 4/1983 | Bolich, Jr. |
| 4,381,919 A | 5/1983 | Jacquet et al. |
| 4,422,853 A | 12/1983 | Jacquet et al. |
| 4,470,982 A | 9/1984 | Winkler |
| 4,507,280 A | 3/1985 | Pohl et al. |
| 4,529,586 A | 7/1985 | Marco et al. |
| 4,536,361 A | 8/1985 | Torobin |
| 4,565,647 A | 1/1986 | Llenado |
| 4,663,158 A | 5/1987 | Wolfram et al. |
| 4,710,374 A | 12/1987 | Grollier et al. |
| 4,822,613 A | 4/1989 | Rodero |
| 4,885,107 A | 12/1989 | Wetzel |
| 4,976,953 A | 12/1990 | Orr et al. |
| 4,990,280 A | 2/1991 | Thorengaard et al. |
| 5,055,384 A | 10/1991 | Kuhnert |
| 5,061,481 A | 10/1991 | Suzuki et al. |
| 5,062,889 A | 11/1991 | Hohl et al. |
| 5,094,853 A | 3/1992 | Hagarty |
| 5,098,636 A | 3/1992 | Balk |
| 5,100,657 A | 3/1992 | Ansher-Jackson et al. |
| 5,100,658 A | 3/1992 | Bolich, Jr. et al. |
| 5,104,646 A | 4/1992 | Bolich, Jr. et al. |
| 5,106,609 A | 4/1992 | Bolich, Jr. et al. |
| 5,166,276 A | 11/1992 | Hayama et al. |
| 5,220,033 A | 6/1993 | Kamei et al. |
| 5,261,426 A | 11/1993 | Kellett et al. |
| 5,280,079 A | 1/1994 | Allen et al. |
| 5,391,368 A | 2/1995 | Gerstein |
| 5,409,703 A | 4/1995 | McAnalley et al. |
| 5,429,628 A | 7/1995 | Trinh et al. |
| 5,457,895 A | 10/1995 | Thompson et al. |
| 5,476,597 A | 12/1995 | Sakata et al. |
| 5,580,481 A | 12/1996 | Sakata et al. |
| 5,582,786 A | 12/1996 | Brunskill et al. |
| 5,660,845 A | 8/1997 | Trinh et al. |
| 5,672,576 A | 9/1997 | Behrens et al. |
| 5,674,478 A | 10/1997 | Dodd et al. |
| 5,750,122 A | 5/1998 | Evans et al. |
| 5,780,047 A | 7/1998 | Kamiya et al. |
| 5,955,419 A | 9/1999 | Barket, Jr. et al. |
| 5,976,454 A | 11/1999 | Sterzel et al. |
| 6,010,719 A | 1/2000 | Remon et al. |
| 6,106,849 A | 8/2000 | Malkan et al. |
| 6,177,391 B1 | 1/2001 | Zafar |
| 6,200,949 B1 | 3/2001 | Reijmer et al. |
| 6,365,142 B1 | 4/2002 | Tamura |
| 6,458,754 B1 | 10/2002 | Velazquez et al. |
| 6,503,521 B1 | 1/2003 | Atis et al. |
| 6,525,034 B2 | 2/2003 | Dalrymple et al. |
| 6,790,814 B1 | 9/2004 | Marin et al. |
| 6,800,295 B2 | 10/2004 | Fox |
| 6,808,375 B2 | 10/2004 | Klotzer |
| 6,825,161 B2 | 11/2004 | Shaefer et al. |
| 6,831,046 B2 | 12/2004 | Carew et al. |
| 6,846,784 B2 | 1/2005 | Engel et al. |
| 6,943,200 B1 | 9/2005 | Corrand et al. |
| 7,015,181 B2 | 3/2006 | Lambino |
| 7,208,460 B2 | 4/2007 | Shefer et al. |
| 7,285,520 B2 | 10/2007 | Krzysik et al. |
| 7,387,787 B2 | 6/2008 | Fox |
| 7,704,328 B2 | 4/2010 | Bailey et al. |
| 7,846,462 B2 | 12/2010 | Spadini et al. |
| 7,901,696 B2 | 3/2011 | Eknoian et al. |
| 8,197,830 B2 | 6/2012 | Helfman et al. |
| 8,268,764 B2 | 9/2012 | Glenn, Jr. et al. |
| 8,273,333 B2 | 9/2012 | Glenn, Jr. et al. |
| 8,546,640 B2 | 10/2013 | Popovsky et al. |
| 9,545,364 B2 | 1/2017 | Glenn, Jr. et al. |
| 10,821,056 B2* | 11/2020 | Swartz .................. A61K 8/442 |
| 2002/0064510 A1 | 5/2002 | Dalrymple et al. |
| 2002/0077264 A1 | 6/2002 | Roberts et al. |
| 2002/0081930 A1 | 6/2002 | Jackson et al. |
| 2002/0098994 A1 | 7/2002 | Zafar |
| 2002/0099109 A1 | 7/2002 | Dufton et al. |
| 2002/0177621 A1 | 11/2002 | Hanada et al. |
| 2002/0187181 A1 | 12/2002 | Godbey et al. |
| 2003/0017208 A1 | 1/2003 | Ignatious et al. |
| 2003/0032573 A1 | 2/2003 | Tanner et al. |
| 2003/0045441 A1 | 3/2003 | Hsu et al. |
| 2003/0069154 A1 | 4/2003 | Hsu et al. |

(56) References Cited

U.S. PATENT DOCUMENTS

| | | |
|---|---|---|
| 2003/0080150 A1 | 5/2003 | Cowan et al. |
| 2003/0099691 A1 | 5/2003 | Lydzinski et al. |
| 2003/0099692 A1 | 5/2003 | Lydzinski et al. |
| 2003/0180242 A1 | 9/2003 | Eccard et al. |
| 2003/0186826 A1 | 10/2003 | Eccard et al. |
| 2003/0194416 A1 | 10/2003 | Shefer et al. |
| 2003/0199412 A1 | 10/2003 | Gupta et al. |
| 2003/0207776 A1 | 11/2003 | Shefer et al. |
| 2003/0209166 A1 | 11/2003 | Vanmaele et al. |
| 2003/0215522 A1 | 11/2003 | Johnson et al. |
| 2003/0232183 A1 | 12/2003 | Dufton |
| 2004/0029762 A1 | 2/2004 | Hensley |
| 2004/0032859 A1 | 2/2004 | Miao |
| 2004/0048759 A1 | 3/2004 | Ribble et al. |
| 2004/0053808 A1 | 3/2004 | Raehse et al. |
| 2004/0071742 A1 | 4/2004 | Popplewell et al. |
| 2004/0071755 A1 | 4/2004 | Fox |
| 2004/0108615 A1 | 6/2004 | Foley |
| 2004/0110656 A1 | 6/2004 | Casey et al. |
| 2004/0126585 A1 | 7/2004 | Kerins et al. |
| 2004/0175404 A1 | 9/2004 | Shefer et al. |
| 2004/0202632 A1 | 10/2004 | Gott et al. |
| 2004/0206270 A1 | 10/2004 | Vanmaele et al. |
| 2004/0242097 A1 | 12/2004 | Hasenoehrl et al. |
| 2004/0242772 A1 | 12/2004 | Huth et al. |
| 2005/0069575 A1 | 3/2005 | Fox |
| 2005/0136780 A1 | 6/2005 | Clark et al. |
| 2005/0137272 A1* | 6/2005 | Gaserod ............ A23L 29/256 521/50 |
| 2005/0202992 A1 | 9/2005 | Portabales et al. |
| 2005/0220745 A1 | 10/2005 | Lu |
| 2005/0232954 A1 | 10/2005 | Yoshinari et al. |
| 2005/0272836 A1 | 12/2005 | Yaginuma et al. |
| 2005/0287106 A1 | 12/2005 | Legendre |
| 2006/0002880 A1 | 1/2006 | Peffly et al. |
| 2006/0013869 A1 | 1/2006 | Ignatious et al. |
| 2006/0052263 A1 | 3/2006 | Roreger et al. |
| 2006/0228319 A1 | 10/2006 | Vona, Jr. et al. |
| 2007/0028939 A1 | 2/2007 | Mareri et al. |
| 2007/0149435 A1 | 6/2007 | Koenig et al. |
| 2007/0225388 A1 | 9/2007 | Cooper et al. |
| 2008/0035174 A1 | 2/2008 | Aubrun-Sonneville et al. |
| 2008/0083420 A1 | 4/2008 | Glenn et al. |
| 2008/0090939 A1 | 4/2008 | Netravali et al. |
| 2008/0131695 A1 | 6/2008 | Aouad et al. |
| 2008/0138492 A1 | 6/2008 | Cingotti |
| 2008/0152894 A1 | 6/2008 | Beihoffer et al. |
| 2008/0215023 A1 | 9/2008 | Scavone et al. |
| 2008/0292669 A1 | 11/2008 | Deng et al. |
| 2008/0293839 A1 | 11/2008 | Stobby |
| 2009/0061225 A1 | 3/2009 | Bailey et al. |
| 2009/0232873 A1 | 9/2009 | Glenn, Jr. et al. |
| 2009/0263342 A1 | 10/2009 | Glenn, Jr. et al. |
| 2010/0167971 A1 | 7/2010 | Glenn, Jr. et al. |
| 2010/0173817 A1 | 7/2010 | Glenn, Jr. et al. |
| 2010/0179083 A1 | 7/2010 | Glenn, Jr. et al. |
| 2010/0279905 A1 | 11/2010 | Glenn, Jr. et al. |
| 2010/0286011 A1 | 11/2010 | Glenn, Jr. et al. |
| 2010/0291165 A1 | 11/2010 | Glenn, Jr. |
| 2010/0298188 A1 | 11/2010 | Glenn, Jr. et al. |
| 2011/0023240 A1 | 2/2011 | Fossum et al. |
| 2011/0027328 A1 | 2/2011 | Baig et al. |
| 2011/0028373 A1 | 2/2011 | Fossum et al. |
| 2011/0028374 A1 | 2/2011 | Fossum et al. |
| 2011/0182956 A1 | 7/2011 | Glenn, Jr. et al. |
| 2011/0189246 A1 | 8/2011 | Glenn, Jr. et al. |
| 2011/0189247 A1 | 8/2011 | Glenn, Jr. et al. |
| 2011/0195098 A1 | 8/2011 | Glenn, Jr. et al. |
| 2011/0250256 A1 | 10/2011 | Hyun-Oh et al. |
| 2012/0021026 A1 | 1/2012 | Glenn, Jr. et al. |
| 2012/0270029 A1 | 10/2012 | Glenn, Jr. et al. |
| 2012/0321580 A1 | 12/2012 | Glenn, Jr. et al. |
| 2013/0236520 A1 | 9/2013 | Popovsky et al. |
| 2013/0303419 A1 | 11/2013 | Glenn, Jr. et al. |
| 2014/0329428 A1 | 11/2014 | Glenn, Jr. et al. |
| 2018/0163325 A1 | 6/2018 | Glenn, Jr. et al. |

FOREIGN PATENT DOCUMENTS

| | | |
|---|---|---|
| CN | 1268558 | 10/2000 |
| CN | 1357613 | 7/2002 |
| CN | 1530431 | 9/2004 |
| CN | 1583991 | 2/2005 |
| DE | 19607851 | 9/1997 |
| DE | 10331767 | 2/2005 |
| EP | 609808 A1 | 8/1994 |
| EP | 0858828 A1 | 8/1998 |
| EP | 1217987 A1 | 7/2002 |
| EP | 1160311 B1 | 3/2006 |
| EP | 1958532 A2 | 8/2008 |
| EP | 2085434 A1 | 8/2009 |
| FR | 2871685 A1 | 12/2005 |
| FR | 2886845 A1 | 12/2006 |
| GB | 2235204 A | 2/1991 |
| GB | 2355008 A1 | 4/2001 |
| JP | 5821609 A | 2/1983 |
| JP | 6272609 A | 4/1987 |
| JP | 6272610 A | 4/1987 |
| JP | 62081462 | 4/1987 |
| JP | 01313418 A | 12/1989 |
| JP | 5344873 A | 12/1993 |
| JP | 0753349 | 2/1995 |
| JP | 789852 A | 4/1995 |
| JP | 10251371 A | 9/1998 |
| JP | 2003073700 A | 3/2003 |
| JP | 2003082397 A | 3/2003 |
| JP | 2004345983 A1 | 12/2004 |
| JP | 2005171063 A1 | 6/2005 |
| JP | 2007091954 A | 4/2007 |
| JP | 2007197540 A | 8/2007 |
| KR | 20020003442 A | 1/2002 |
| WO | WO8301943 A1 | 11/1992 |
| WO | 0617083 A1 | 1/1994 |
| WO | WO9514495 A1 | 6/1995 |
| WO | WO2001019948 A1 | 3/2001 |
| WO | WO0125393 A1 | 4/2001 |
| WO | WO200125322 A1 | 4/2001 |
| WO | WO2001024770 A1 | 4/2001 |
| WO | WO2001054667 A1 | 8/2001 |
| WO | WO2004032859 A1 | 4/2004 |
| WO | WO2004041991 A1 | 5/2004 |
| WO | WO2005003423 A1 | 1/2005 |
| WO | WO2007033598 A1 | 3/2007 |
| WO | WO2007093558 A1 | 8/2007 |
| WO | WO2009019571 A1 | 2/2009 |

OTHER PUBLICATIONS

International Search Report for PCT/US2009/040739 dated Aug. 17, 2009.

International Search Report for PCT/US2009/040739 dated Nov. 4, 2009.

International Search Report for PCT/US2009/067087 dated Dec. 15, 2011.

International Search Report for PCT/US2009/067130 dated Jul. 19, 2011.

International Search Report for PCT/US2009/067088 dated Jul. 19, 2011.

International Search Report for PCT/US2009/067088 dated May 4, 2011.

International Search Report for PCT/US2009/067080 dated Apr. 29, 2011.

International Search Report for PCT/US2009/067131 dated Jul. 20, 2011.

International Search Report for PCT/US2009/067132 dated May 9, 2011.

International Search Report for PCT/US2009/067133 dated Jul. 19, 2011.

International Search Report for PCT/US2010/059365 dated Apr. 27, 2011.

(56) References Cited

OTHER PUBLICATIONS

International Search Report for PCT/US2010/059455 dated Apr. 27, 2011.
International Search Report for PCT/US2010/059441 dated Jun. 7, 2013.
International Search Report for PCT/US2010/059359 dated Apr. 27, 2011.
International Search Report for PCT/US2011/042640 dated Feb. 20, 2013.
International Search Report for PCT/US2012/032253 dated Jul. 20, 2012.
Anonymous "P8136 Poly(vinyl alcohol)" Internet article, [Online] XP002538935 retrieved from the Internet: URL:http/www.sigmaaldrich.com/catalog/ProductDetail.do?D7=0%N25-SEARCH_CONCAT_PNO|BRAND_KEY%N4=P8136%7SCIAL%N25=0%QS=0N%F=SPEC retrieved on Jul. 28, 2009.
Encyclopedia of Polymer Science and Engineering, vol. 15, 2nd ed., p. 204 308 Silicones, 1989.
Hildebrand, T., et al. "Quantification of bone microarchitecture with the structure mode index", Comp Meth Biomech Biomed Eng 1997; 1:15-23.
Vaughan, C.D. "Solubility, Effects in Product, Package, Penetration and Preservation", Cosmetics and Toiletries, vol. 103, Oct. 1988.
Vesterby, A.: "Star Volume in Bone Research: A Histomorphometric Analysis Of Trabecular Bone Structure Using Vertical Sections", Anat Rec: Feb. 1993, 232(2):325-334.
All Office Actions for U.S. Appl. No. 13/597,539, filed Aug. 29, 2012.
All Office Actions for U.S. Appl. No. 12/424,812, filed Apr. 16, 2009.
All Office Actions for U.S. Appl. No. 12/633,257, filed Dec. 8, 2009.
All Office Actions for U.S. Appl. No. 12/633,301, filed Dec. 8, 2009.
All Office Actions for U.S. Appl. No. 12/633,550, filed Dec. 8, 2009.
All Office Actions for U.S. Appl. No. 12/633,335, filed Dec. 8, 2009.
All Office Actions for U.S. Appl. No. 12/633,415, filed Dec. 8, 2009.
All Office Actions for U.S. Appl. No. 13/561,298, filed Jul. 30, 2012.
All Office Actions for U.S. Appl. No. 12/633,572, filed Dec. 8, 2009.
All Office Actions for U.S. Appl. No. 12/361,634, filed Jan. 29, 2009.
All Office Actions for U.S. Appl. No. 12/962,846, filed Dec. 8, 2010.
All Office Actions for U.S. Appl. No. 12/962,873, filed Dec. 8, 2010.
All Office Actions for U.S. Appl. No. 12/962,888, filed Dec. 8, 2010.
All Office Actions for U.S. Appl. No. 12/962,905, filed Dec. 8, 2010.
All Office Actions for U.S. Appl. No. 13/440,475, filed Apr. 5, 2012.
All Office Actions for U.S. Appl. No. 13/915,797, filed Jun. 12, 2013.
All Office Actions for U.S. Appl. No. 12/633,228, filed Dec. 8, 2009.
All Office Actions for U.S. Appl. No. 13/173,639, filed Jun. 30, 2011.
All Office Actions for U.S. Appl. No. 14/334,862, filed Jul. 18, 2014.
All Office Actions for U.S. Appl. No. 15/170,125, filed Jun. 1, 2016.
All Office Actions for U.S. Appl. No. 13/173,639, filed Dec. 9, 2016All Office Actions for U.S. Appl. No. 13/173,639, filed Jun. 30, 2011.

* cited by examiner

FIGURE 4C
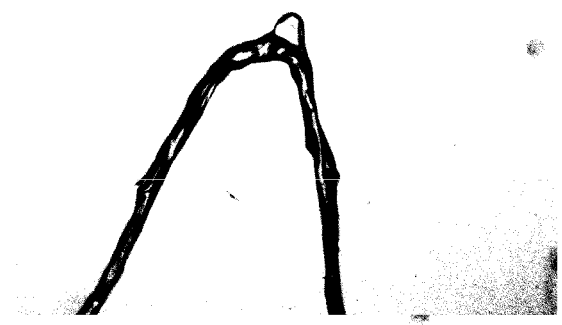
0.0 second
0.4 second
0.6 second
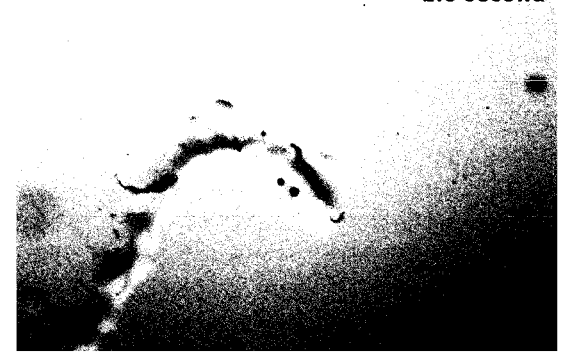
1.0 second

DISSOLVABLE FIBROUS WEB STRUCTURE ARTICLE COMPRISING ACTIVE AGENTS

FIELD OF THE INVENTION

Described herein, is a personal care, oral care, health care, and household care composition that delivers active agents onto hair, hair follicles, skin, teeth, the oral cavity, fabric and hard surfaces in the form of an article that is a dissolvable fibrous web structure.

BACKGROUND OF THE INVENTION

A majority of consumer products in the market today are sold as liquid products. While widely used, liquid products have disadvantages in terms of packaging, storage, transportation, and convenience of use.

Liquid consumer products typically are sold in bottles which add significant cost as well as packaging waste, much of which ends up in land-fills.

Traditionally delivery of active agents from multicomponent fibers are the result of fibers comprised of typical thermoplastic polymers, such as polyolefins, which are insoluble in water, i.e., the fiber does not fully dissolve. Furthermore, the active agent component of such fibers traditionally incorporates active agents only as a minor proportion, for example, up to about 5% by weight.

The production of micron and sub-micron dissolvable fibers (and corresponding webs therefrom) from aqueous processing mixtures comprising active agents and water soluble polymers would be advantageous due to the very high surface area to weight ratio (immediately after spinning the fibers) which would significantly reduce the drying energy and time required to produce the solid form while still providing a highly open pore structure required for potentially fast dissolution rates. However, the inclusion of active agents can adversely affect the extensional rheology properties of the water soluble polymer composition and the ability to produce fibers. Traditionally, fibers from poly(vinyl alcohol) solutions have included incorporation of minor/low levels of ingredients such as plasticizers (polyethylene glycol, glycerin), extenders (clay, starch), and cross-linking agents all of which are generally known to be compatible with fiber forming processes. However, including high levels of of ionic surfactants (anionic surfactants, amphoteric surfactants, zwitterionic surfactants, cationic surfactants) can be difficult as they may result in generally non-cohesive liquid/paste-like phase structures (worm-like micelle, liquid crystal, and hexagonal phases) even at high concentrations.

The present inventors have surprisingly discovered the ability to produce dissolvable fibers comprising significant levels of active agents, including ionic surfactants. In certain instances, an extensional rheology modifier is included within the compositions to enhance the fiber formation ability in the presence of active agents.

It is therefore an object of the present composition to provide a dissolvable fibrous consumer product that can be conveniently and quickly dissolved in the palm of the consumer to reconstitute a liquid product for ease of application to the target consumer substrate while providing sufficient delivery of active agents for the intended effect on the target consumer substrates (with similar performance as today's liquid products). It is a further object to provide such a product that can be produced in an economical manner by spinning fibers comprising the active agents.

SUMMARY OF THE INVENTION

An article comprising a dissolvable fibrous web structure comprising a significant number of fibers with average diameter less than about 10 microns. The fibers are made from a composition comprising: from about 10% to about 75% of a surfactant; from about 10% to about 70% water soluble polymeric structurant; and from about 1% to about 25% plasticizer; wherein the ratio of the water soluble polymeric structurant to the active agent in the fiber is 3.5 or less.

BRIEF DESCRIPTION OF THE DRAWINGS

While the specification concludes with claims which particularly point out and distinctly claim the present invention, it is believed that the present invention will be better understood from the following description of embodiments, taken in conjunction with the accompanying drawings, in which like reference numerals identify identical elements and wherein:

FIG. 4C is a Microscopic Dissolution Investigation of Spunbond Fibers.

DETAILED DESCRIPTION OF THE INVENTION

Figure 1:
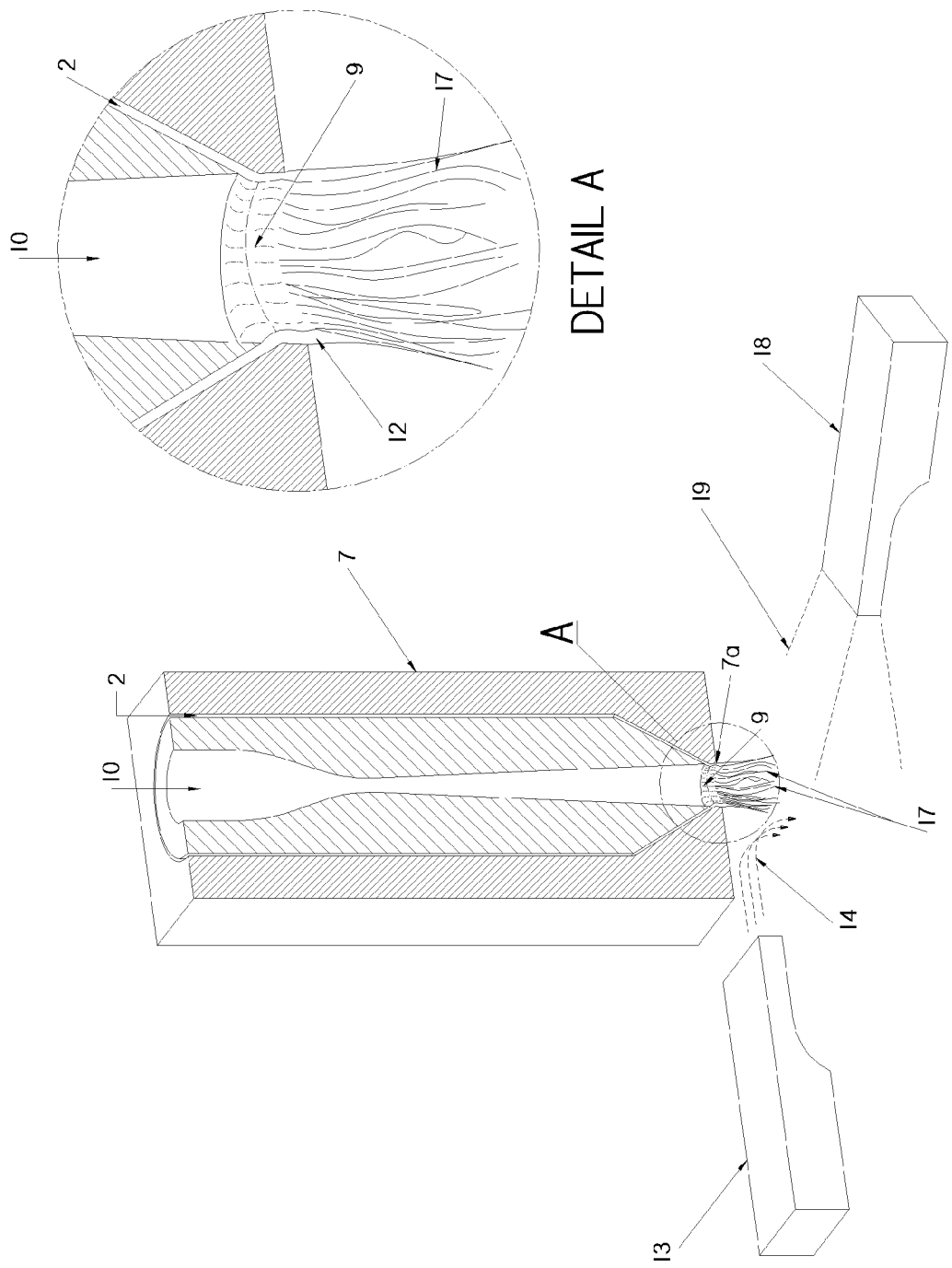
FIG. 1 is a schematic of a circular fluid film fibrillation nozzle for forming fibers of the processing mixture fluid.

In all embodiments of the present invention, all percentages are by weight of the total composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about one atmosphere of pressure and at about 50% relative humidity. All such weights as they pertain to listed ingredients are based on the active level and do not include carriers or by-products that may be included in commercially available materials, unless otherwise specified.

Definitions

As used herein, the term "hair care composition" means a composition that may be applied to mammalian hair and skin without undue undesirable effects.

The fibrous dissolvable web structure article may be referred to herein as "the Article" or "the Dissolvable Article". All references are intended to mean the dissolvable fibrous web structure article. A "Consumer Product Article"

as used herein means the Article which delivers a consumer desired benefit, most likely through the use of a benefit agent and/or active, for example a beauty care agent.

As used herein, "dissolvable" means that the Article meets the hand dissolution value. In one embodiment the Article has a hand dissolution value of from about 1 to about 30 strokes, in another embodiment from about 2 to about 25 strokes, in another embodiment from about 3 to about 20 strokes, and in still another embodiment from about 4 to about 15 strokes as measured by the Hand Dissolution Method.

The Article may constitute one or more layers of fibrous web which are optionally bonded together via a bonding means (including heat, moisture, ultrasonic, pressure etc.).

The Article has a basis weight of from about 30 grams/m$^2$ to about 1,000 grams/m$^2$, in another embodiment from about 60 grams/m$^2$ to about 800 grams/m$^2$, in an another embodiment from about 90 grams/m$^2$ to about 700 grams/m$^2$, and in still another embodiment from about 120 grams/m$^2$ to about 650 grams/m$^2$; and a thickness as defined herein of from about 0.25 mm to about 10 mm, in one embodiment from about 0.5 mm to about 7 mm, and in an another embodiment from about 0.75 mm to about 6 mm.

The Article comprises a significant number of dissolvable fibers with an average diameter less than about 150 micrometer, in one embodiment than about 100 micrometer, in an another embodiment than about 10 micrometer, and in an yet another embodiment than about 1 micrometer with a relative standard deviation of less than 100%, alternatively less than 80%, alternatively less than 60%, alternatively less than 50%, such as in the range of 10% to 50%, for example. As set forth herein, the significant number means at least 10% of all the dissolvable fibers, in an another embodiment at least 25% of all the dissolvable fibers, in another embodiment at least 50% of all the dissolvable fibers, in yet another embodiment at least 75% of all the dissolvable fibers. In a particular embodiment, the significant number may be at least 99% of all the dissolvable fibers. In a further embodiment, at least 50% of all the dissolvable fibers may have an average diameter less than about 10 micrometer. The dissolvable fibers produced by the method of the present disclosure have a significant number of dissolvable fibers with an average diameter less than about 1 micrometer, or sub-micron fibers. In an embodiment, the article comprising Article may have at least 25% of all the dissolvable fibers with an average diameter less than about 1 micrometer, in another embodiment at least 35% of all the dissolvable fibers with an average diameter less than about 1 micrometer, in another embodiment at least 50% of all the dissolvable fibers with an average diameter less than about 1 micrometer, and in yet another embodiment at least 75% of all the dissolvable fibers with an average diameter less than about 1 micrometer.

As used herein, the "average diameter" is calculated an arithmetic mean of diameters of all the dissolvable fibers in the sample measured. The relative standard deviation of fiber diameter is calculated by dividing the statistical standard deviation of the diameter by the average diameter of all the fibers in the measured sample. The method of measuring fiber diameter is described later in the disclosure.

The Basis Weight of the Article herein is calculated as the weight of the Article per area of the Article (grams/m$^2$). The area is calculated as the projected area onto a flat surface perpendicular to the outer edges of the Article. For a flat object, the area is thus computed based on the area enclosed within the outer perimeter of the sample. For a spherical object, the area is thus computed based on the average diameter as $3.14 \times (diameter/2)^2$. For a cylindrical object, the area is thus computed based on the average diameter and average length as diameter×length. For an irregularly shaped three dimensional object, the area is computed based on the side with the largest outer dimensions projected onto a flat surface oriented perpendicularly to this side. This can be accomplished by carefully tracing the outer dimensions of the object onto a piece of graph paper with a pencil and then computing the area by approximate counting of the squares and multiplying by the known area of the squares or by taking a picture of the traced area (preferably shaded-in for contrast) including a scale and using image analysis techniques.

The thickness of the Article is obtained using a micrometer or thickness gage, such as the Mitutoyo Corporation Digital Disk Stand Micrometer Model Number IDS-1012E (Mitutoyo Corporation, 965 Corporate Blvd, Aurora, Ill., USA 60504). The micrometer has a 1 inch diameter platen weighing about 32 grams, which measures thickness at an application pressure of about 40.7 psi (6.32 gm/cm$^2$).

The thickness of the Article is measured by raising the platen, placing a section of the Article sample on the stand beneath the platen, carefully lowering the platen to contact the sample, releasing the platen, and measuring the thickness of the sample in millimeters on the digital readout. The sample should be fully extended to all edges of the platen to make sure thickness is measured at the lowest possible surface pressure, except for the case of more rigid samples which are not flat. For more rigid samples which are not completely flat, a flat edge of the sample is measured using only one portion of the platen impinging on the flat portion of the sample.

The Article has a dry density of from about 0.01 g/cm$^3$ to about 0.6 g/cm$^3$, in one embodiment from about 0.03 g/cm$^3$ to about 0.5 g/cm$^3$, in one embodiment from about 0.04 g/cm$^3$ to about 0.4 g/cm$^3$, and in an another embodiment from about 0.06 g/cm$^3$ to about 0.3 g/cm$^3$.

The dry density of the Article is determined by the equation: Calculated Density=Basis Weight of Article/(Article Thickness×1,000). The Basis Weight and Thickness of the Article are determined in accordance with the methodologies described herein.

"Personal care composition," as used herein, means a composition that may be applied to mammalian keratinous tissue without undue undesirable effects.

"Keratinous tissue," as used herein, means keratin-containing layers disposed as the outermost protective covering of mammals and includes, but is not limited to, skin, hair, scalp and nails.

"Beauty benefit," as used herein in reference to mammalian keratinous tissue includes, but is not limited to, cleansing, sebum inhibition, reducing the oily and/or shiny appearance of skin and/or hair, reducing dryness, itchiness and/or flakiness, reducing skin pore size, exfoliation, desquamation, improving the appearance of the keratinous tissue, conditioning, smoothening, etc.

"Beauty benefit agent," as used herein, refers to materials that can be included in the composition to deliver one or more Beauty benefits.

"Skin care actives," or "actives," as used herein, means compounds that, when applied to the skin, provide a benefit or improvement to the skin. It is to be understood that skin care actives are useful not only for application to skin, but also to hair, scalp, nails and other mammalian keratinous tissue.

The Articles described herein can be useful for treating keratinous tissue (e.g., hair, skin, or nails) condition. As used herein, "treating" or "treatment" or "treat" includes regulating and/or immediately improving keratinous tissue cosmetic appearance and/or feel. For instance, "regulating skin, hair, or nail condition" includes: thickening of skin, hair, or nails (e.g, building the epidermis and/or dermis and/or sub-dermal [e.g., subcutaneous fat or muscle] layers of the skin, and where applicable the keratinous layers of the nail and hair shaft) to reduce skin, hair, or nail atrophy, increasing the convolution of the dermal-epidermal border (also known as the rete ridges), preventing loss of skin or hair elasticity (loss, damage and/or inactivation of functional skin elastin) such as elastosis, sagging, loss of skin or hair recoil from deformation; melanin or non-melanin change in coloration to the skin, hair, or nails such as under eye circles, blotching (e.g., uneven red coloration due to, e.g., rosacea) (hereinafter referred to as "red blotchiness"), sallowness (pale color), discoloration caused by telangiectasia or spider vessels, and graying hair.

Consumer Product Article

The present inventors have surprisingly discovered that a Consumer Product Article formed from a fibrous web can be produced wherein each fiber comprises a significant level of one or more active and/or agents via a fiber spinning process. This can now be accomplished by preparing a processing mixture comprising active and/or agent, dissolved water soluble polymeric structurant, and optionally plasticizer and spinning the composition in the presence of a pressurized gas stream (preferably heated air) to remove the majority of the water and produce solid fibers; and forming the fibers into a web, including optional bonding techniques, with a desired final moisture content, in one embodiment from about 0.5% to about 15% moisture, to form the Consumer Product Article.

It was found that fibers can be produced which comprise a significant level of active/agents, especially when the active/agent encompasses an ionic surfactant system which are generally known to form non-cohesive liquid/paste-like phase structures, especially at higher concentrations, and would thereby hinder the ability to produce fibers. The ability of the ionic surfactant system to produce highly elongated micelles (typically with a significant percentage of amphoteric surfactants and/or zwitterionic surfactants in synergy with anionic surfactants) may result in synergy with the water soluble water soluble polymeric structurant resulting in sufficient viscoelasticity and extensional rheology (stringiness) to generate the fibers.

In an additional embodiment, an extensional rheology modifier may be incorporated within the processing mixture composition.

The fibers disclosed herein comprise a water soluble polymeric structurant and an active agent wherein the weight ratio of the water soluble polymeric structurant to the active/agent in the fibers is about 3.5 or less and/or less than about 2.5 and/or less than about 1.5 and/or less than about 1.0 and/or less than about 0.5 and/or less than about 0.3 and/or to about 0.1 and/or to about 0.15 and/or to about 0.2.

I. COMPOSITION

The Articles described herein may be lathering or non-lathering under consumer relevant usage instructions.
A. Lathering Articles
Lathering Articles for the purposes of lathering and/or cleaning comprise from about 10% to about 75%, in one embodiment from about 30% to about 70%, and in another embodiment from about 40% to about 65% by weight of the personal care article of surfactant; wherein the surfactant comprises one or more surfactants from Group I, wherein Group I includes anionic surfactants which are suitable for use in hair care or other personal care compositions, and optionally one or more surfactants from Group II, wherein Group II includes a surfactant selected from the group consisting of amphoteric, zwitterionic and combinations thereof suitable for use in hair care or other personal care compositions; wherein the ratio of Group I to Group II surfactants is from about 100:0 to about 30:70. In another embodiment the ratio of Group I to Group II surfactants is from about 85:15 to about 40:60. In yet another embodiment the ratio of Group I to Group II surfactants is from about 70:30 to about 55:45.

Non limiting examples of anionic surfactants are described in U.S. Pat. Nos. 2,486,921; 2,486,922; and 2,396,278. The anionic surfactant can be selected from the group consisting of alkyl and alkyl ether sulfates, sulfated monoglycerides, sulfonated olefins, alkyl aryl sulfonates, primary or secondary alkane sulfonates, alkyl sulfosuccinates, acid taurates, acid isethionates, alkyl glycerylether sulfonate, sulfonated methyl esters, sulfonated fatty acids, alkyl phosphates, acyl glutamates, acyl sarcosinates, alkyl lactylates, anionic fluorosurfactants, sodium lauroyl glutamate, and combinations thereof.

Non limiting examples of suitable zwitterionic or amphoteric surfactants are described in U.S. Pat. No. 5,104,646 (Bolich Jr. et al.), U.S. Pat. No. 5,106,609 (Bolich Jr. et al.). The zwitterionic surfactant can be selected from the group consisting of cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, and lauryl sultaine. The amphoteric surfactant can be selected from the group consisting of sodium cocoamphoacetate, sodium cocoamphodiacetate, sodium lauroamphoacetate, sodium lauroamphodiacetate, ammonium lauroamphoacetate, ammonium cocoamphoacetate, triethanolamine lauroamphoacetate, and triethanolamine cocoamphoacetate.

Additional suitable Group I and Group II surfactants include those disclosed in U.S. Patent Application No. 61/120,765 and those surfactants disclosed in McCutcheon's Detergents and Emulsifiers, North American Edition (1986), Allured Publishing Corp.; McCutcheon's, Functional Materials, North American Edition (1992), Allured Publishing Corp.; and U.S. Pat. No. 3,929,678 (Laughlin et al.). Other non-limiting examples of suitable surfactants are included in U.S. Ser. No. 61/120,790.
B. Non-Lathering Articles
The non-lathering Articles comprise from about 10% to about 75%, in another embodiment from about 15% to about 60%, and in another embodiment from about 20% to about 50% by weight of the personal care article of surfactant; wherein the surfactant comprises one or more of the surfactants described below, however, wherein the anionic surfactants are included at a level less of less than about 10%.
1. Anionic Surfactants
If the Article is non lathering, the substrate may comprise a maximum level of about 10% (or less than about 10%) of anionic surfactants.

2. Non-Ionic Surfactants

The non-lathering Articles comprise from about 10% to about 75%, in another embodiment from about 15% to about 60%, and in another embodiment from about 20% to about 50% by weight of the personal care article of non-ionic surfactants. In one embodiment non-ionic surfactants are included as a process aid in making a stable Article. Suitable nonionic surfactants for use include those described in McCutcheon's Detergents and Emulsifiers, North American edition (1986), Allured Publishing Corp., and McCutcheon's Functional Materials, North American edition (1992). Suitable nonionic surfactants for use in the personal care compositions include, but are not limited to, polyoxyethylenated alkyl phenols, polyoxyethylenated alcohols, polyoxyethylenated polyoxypropylene glycols, glyceryl esters of alkanoic acids, polyglyceryl esters of alkanoic acids, propylene glycol esters of alkanoic acids, sorbitol esters of alkanoic acids, polyoxyethylenated sorbitor esters of alkanoic acids, polyoxyethylene glycol esters of alkanoic acids, polyoxyethylenated alkanoic acids, alkanolamides, N-alkylpyrrolidones, alkyl glycosides, alkyl polyglucosides, alkylamine oxides, and polyoxyethylenated silicones.

3. Cationic Surfactants

The non-lathering Articles comprise from about 10% to about 75%, in another embodiment from about 15% to about 60%, and in another embodiment from about 20% to about 50% by weight of the personal care article of cationic surfactants. In one embodiment cationic surfactants are included as a process aid in making an Article. Suitable cationic surfactants for use include those described in McCutcheon's Detergents and Emulsifiers, North American edition (1986), Allured Publishing Corp., and McCutcheon's Functional Materials, North American edition (1992). Suitable quaternary ammonium cationic conditioner actives can include cetyltrimethylammonium chloride, behenyltrimethylammonium chloride (BTAC), stearyltrimethylammonium chloride, cetylpyridinium chloride, octadecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, distearyldimethylammonium chloride, tallowtrimethylammonium chloride, cocotrimethylammonium chloride, dipalmitoylethyldimethylammonium chloride, PEG-2 oleylammonium chloride and salts of these, where the chloride is replaced by halogen, (e.g., bromide), acetate, citrate, lactate, glycolate, phosphate nitrate, sulphate, or alkylsulphate.

In one embodiment, the quaternary ammonium cationic conditioner actives for use in the invention are cetyltrimethylammonium chloride, available commercially, for example as GENAMIN CTAC by Clariant and Arquad 16/29 supplied by Akzo Nobel, behenyltrimethylammonium chloride (BTMAC) such as GENAMIN KDMP supplied by Clariant, and distearyldimethylammonium chloride such as GENAMIN DSAP supplied by Clariant. Mixtures of any of the foregoing materials may also be suitable. In another embodiment, the quaternary ammonium cationic conditioner active is behenyltrimethylammonium chloride (BTMAC).

4. Polymeric Surfactants

Polymeric surfactants can also be surfactants to be employed as a process aid in making the Article, either alone or in combination with ionic and/or nonionic surfactants. Suitable polymeric surfactants for use in the personal care compositions include, but are not limited to, block copolymers of ethylene oxide and fatty alkyl residues, block copolymers of ethylene oxide and propylene oxide, hydrophobically modified polyacrylates, hydrophobically modified celluloses, silicone polyethers, silicone copolyol esters, diquaternary polydimethylsiloxanes, and co-modified amino/polyether silicones.

C. Additional Components

1. Water-Soluble Polymer ("Polymer Structurant")

The Article comprises water-soluble polymers that function as a structurant. As used herein, the term "water-soluble polymer" is broad enough to include both water-soluble and water-dispersible polymers, and is defined as a polymer with a solubility in water, measured at 25° C., of at least about 0.1 gram/liter (g/L). In some embodiments, the polymers have solubility in water, measured at 25° C., of from about 0.1 gram/liter (g/L). to about 500 grams/liter (g/L). (This indicates production of a macroscopically isotropic or transparent, colored or colorless solution). The polymers for making these Articles may be of synthetic or natural origin and may be modified by means of chemical reactions. They may or may not be film-forming. These polymers should be physiologically acceptable, i.e., they should be compatible with the skin, mucous membranes, the hair and the scalp.

The one or more water-soluble polymers may be present from about 10% to about 70% by weight of the Article, in one embodiment from about 15% to about 60% by weight of the Article, and in another embodiment from about 20% to about 50% by weight of the Article, and in yet another embodiment from about 25% to about 40% by weight of the Article.

The one or more water-soluble polymers can be selected such that their weighted average molecular weight is from about 40,000 to about 500,000, in one embodiment from about 50,000 to about 400,000, in yet another embodiment from about 60,000 to about 300,000, and in still another embodiment from about 70,000 to about 200,000. The weighted average molecular weight is computed by summing the average molecular weights of each polymer raw material multiplied by their respective relative weight percentages by weight of the total weight of polymers present within the Article.

In one embodiment, at least one of the one or more water-soluble polymers is chosen such that about 2% by weight solution of the water-soluble polymer gives a viscosity at 20° C. of from about 4 centipoise to about 80 centipoise; in an another embodiment from about 5 centipoise to about 70 centipoise; and in another embodiment from about 6 centipoise to about 60 centipoise.

The water-soluble polymer(s) can include, but are not limited to, synthetic polymers as described in U.S. Ser. No. 61/120,786 including polymers derived from acrylic monomers such as the ethylenically unsaturated carboxylic monomers and ethylenically unsaturated monomers as described in U.S. Pat. No. 5,582,786 and EP-A-397410. The water-soluble polymer(s) which are suitable may also be selected from naturally sourced polymers including those of plant origin examples which are described in U.S. Ser. No. 61/120,786. Modified natural polymers are also useful as water-soluble polymer(s) and are included in U.S. Ser. No. 61/120,786. In one embodiment, water-soluble polymers include polyvinyl alcohols, polyacrylates, polymethacrylates, copolymers of acrylic acid and methyl acrylate, polyvinylpyrrolidones, polyalkylene oxides, starch and starch derivatives, pullulan, gelatin, hydroxypropylmethylcelluloses, methylcelluloses, and carboxymethycelluloses. In another embodiment, water-soluble polymers include polyvinyl alcohols, and hydroxypropylmethylcelluloses. Suitable polyvinyl alcohols include those available from Celanese Corporation (Dallas, Tex.) under the CELVOL® trade name. Suitable hydroxypropylmethylcelluloses include those available from the Dow Chemical Company (Midland, Mich.) under the METHOCEL® trade name.

In a particular embodiment, the above mentioned water-soluble polymer(s) may be blended with any single starch or combination of starches as a filler material in such an amount as to reduce the overall level of water-soluble polymers required, so long as it helps provide the personal care article with the requisite structure and physical/chemical characteristics as described herein.

In such instances, the combined weight percentage of the water-soluble polymer(s) and starch-based material generally ranges from about 10% to about 50%, in one embodiment from about 15% to about 40%, and in a particular embodiment from about 20% to about 30% by weight relative to the total weight of the Article. The weight ratio of the water-soluble polymer(s) to the starch-based material can generally range from about 1:10 to about 10:1, in one embodiment from about 1:8 to about 8:1, in still another embodiment from about 1:7 to about 7:1, and in yet another embodiment from about 6:1 to about 1:6.

Typical sources for starch-based materials can include cereals, tubers, roots, legumes and fruits. Native sources can include corn, pea, potato, banana, barley, wheat, rice, sago, amaranth, tapioca, arrowroot, canna, sorghum, and waxy or high amylase varieties thereof. The starch-based materials may also include native starches that are modified using any modification known in the art, including those described in U.S. Ser. No. 61/120,786.

2. Plasticizer

The Article described herein may further comprise a water soluble plasticizing agent suitable for use in personal care compositions. In one embodiment, the one or more plasticizers may be present from about 1% to about 25% by weight of the Article; in another embodiment from about 3% to about 20%; in another embodiment from about 5% to about 15%. Non-limiting examples of suitable plasticizing agents include polyols, copolyols, polycarboxylic acids, polyesters and dimethicone copolyols. Examples of useful polyols include, but are not limited to, glycerin, diglycerin, propylene glycol, ethylene glycol, butylene glycol, pentylene glycol, cyclohexane dimethanol, hexane diol, polyethylene glycol (200-600), sugar alcohols such as sorbitol, manitol, lactitol and other mono- and polyhydric low molecular weight alcohols (e.g., C2-C8 alcohols); mono di- and oligo-saccharides such as fructose, glucose, sucrose, maltose, lactose, and high fructose corn syrup solids and ascorbic acid. Suitable examples of polycarboxylic acids for use herein are disclosed in U.S. Ser. No. 61/120,786.

In one embodiment, the plasticizers include glycerin or propylene glycol and combinations thereof. European Patent Number EP283165B1 discloses other suitable plasticizers, including glycerol derivatives such as propoxylated glycerol.

3. Extensional Rheology Modifier

The Article may comprise an extensional rheology modifier. The extensional rheology modifier may be combined with the aforementioned water soluble water soluble polymeric structurants to obtain rheological properties desirable for fiber formation. The rheological properties critical for fiber formation comprise: shear viscosity, elongational viscosity, elasticity, and so forth.

The weight-average molecular weight of the extensional rheology modifier may be from about 500,000 to about 10,000,000, in one embodiment from about 1,000,000 to about 8,000,000, and in another embodiment from about 2,000,000 to about 6,000,000. The extensional rheology modifier, may be present from about 0 wt % to about 5 wt %, by weight of the Article of an extensional rheology modifier, alternatively from about 0.1 wt % to about 4 wt %, in one embodiment from about 0.25 wt % to about 3 wt %, and in another embodiment from about 0.5 wt % to about 2 wt % by weight of the Article of an extensional rheology modifier. In such instances, the weight percentage of the extensional rheology modifier may be less than about 10%, in another embodiment less than 5%, and in yet another embodiment less 2% by weight of the processing mixture forming the Article.

In one embodiment, two or more extensional rheology modifiers of differing molecular weights may be combined in various ratios in an embodiment to get a desired weight-average molecular weight and overall molecular weight distribution suitable for forming fibers, provided that each of the individually sourced polymers has a weight-average molecular weight of from about 500,000 to about 10,000,000. In an embodiment, a high weight-average molecular weight polymer may be combined with a low weight-average molecular weight polymer to obtain rheological properties, such as shear viscosity, elongational viscosity, and elasticity of the processing mixture desirable for fiber formation. One ordinary skilled in the art of fiber forming may be able to optimize the ratio of the high and low weight-average molecular weight polyethylene oxide to obtain desirable fiber forming rheological properties.

The extensional rheology modifiers may be selected from polyvinyl alcohols, polyvinylpyrrolidones, polyalkylene oxides, polyacrylates, caprolactams, polymethacrylates, polymethylmethacrylates, polyacrylamides, polymethylacrylamides, polydimethylacrylamides, polyethylene glycol monomethacrylates, polyurethanes, polycarboxylic acids, polyvinyl acetates, polyesters, polyamides, polyamines, polyethyleneimines, maleic/(acrylate or methacrylate) copolymers, copolymers of methylvinyl ether and of maleic anhydride, copolymers of vinyl acetate and crotonic acid, copolymers of vinylpyrrolidone and of vinyl acetate, copolymers of vinylpyrrolidone and of caprolactam, vinyl pyrollidone/vinyl acetate copolymers, copolymers of anionic, cationic and amphoteric monomers, karaya gum, tragacanth gum, gum Arabic, acemannan, konjac mannan, acacia gum, gum ghatti, whey protein isolate, and soy protein isolate; seed extracts including guar gum, locust bean gum, quince seed, and psyllium seed; seaweed extracts such as Carrageenan, alginates, and agar; fruit extracts (pectins); those of microbial origin including xanthan gum, gellan gum, pullulan, hyaluronic acid, chondroitin sulfate, and dextran; and those of animal origin including casein, gelatin, keratin, keratin hydrolysates, sulfonic keratins, albumin, collagen, glutelin, glucagons, gluten, zein, shellac, cellulose derivatives such as hydroxypropylmethylcellulose, hydroxymethylcellulose, hydroxyethylcellulose, methylcellulose, hydroxypropylcellulose, ethylcellulose, carboxymethylcellulose, cellulose acetate phthalate, nitrocellulose and other cellulose ethers/esters; guar derivatives such as hydroxypropyl guar; and combinations thereof.

In one embodiment the extensional rheology modifiers include polyethylene oxides.

In a another embodiment, an about 8,000,000 weight-average molecular weight polyethylene oxide may be combined with an about 1,000,000 weight-average molecular weight polyethylene oxide in ratios ranging from about 5:95 to about 95:5 by weight. In another embodiment, an about 6,000,000 weight-average molecular weight polyethylene oxide may be combined with an about 2,000,000 weight-average molecular weight polyethylene oxide in ratios ranging from about 5:95 to about 95:5 by weight. In still another embodiment, an about 10,000,000 weight-average molecular weight polyethylene oxide may be combined with an about 1,000,000 weight-average molecular weight polyethylene oxide in ratios ranging from about 1:99 to about 99:1 by weight. Without being bound by any one theory, combining a small percentage of very high molecular weight polymer such as an about 10,000,000 molecular weight polyethylene oxide with lower molecular weight polymer such as with an about 1,000,000 molecular weight polyethylene oxide provides elasticity and high elongational viscosity while minimally impacting the shear viscosity of a polymer solution or melt to form fibers. The combining ratio of high and low molecular weight polymers depends on overall rheological properties and surface tension of the processing mixture, and processing conditions of fiber formation.

4. Optional Ingredients

The Article may further comprise other optional ingredients that are known for use or otherwise useful in consumer product compositions, provided that such optional materials are compatible with the selected essential materials described herein, or do not otherwise unduly impair the performance of the composition.

The optional ingredients may comprise active/agents which may be selected from the group consisting of: personal cleansing and/or conditioning agents such as hair care agents, hair conditioning agents, skin care agents, and skin conditioning agents; laundry care and/or conditioning agents such a fabric care agents, fabric conditioning agents, fabric softening agents, fabric anti-wrinkling agents, fabric care anti-static agents, fabric care stain removal agents, soil release agents, dispersing agents, suds suppressing agents, anti-foam agents, and fabric refreshing agents; hard surface care and/or conditioning agents such as liquid dishwashing agents, powder dishwashing agents, polishing agents, antimicrobial agents, perfume, bleaching agents (such as oxygen bleaching agents, hydrogen peroxide, percarbonate bleaching agents, perborate bleaching agents, chlorine bleaching agents), bleach activating agents, chelating agents, builders, brightening agents, dye transfer-inhibiting agents, water-softening agents, water-hardening agents, pH adjusting agents, acids, bases, medicinal agents, lotions, teeth whitening agents, tooth care agents, mouthwash agents, periodontal gum care agents, sunscreen agents, enzymes, flocculating agents, effervescent agents, preservatives, cosmetic agents, make-up removal agents, lathering agents, deposition aid agents, coacervate-forming agents, clays, thickening agents, latexes, silicas, drying agents, water-treatment agents, odor control agents, antiperspirant agents, cooling agents, warming agents, absorbent gel agents, anti-inflammatory agents, dyes, pigments, edible agents, dietary agents, vitamins, minerals, and combinations thereof.

The optional ingredients may also include those materials approved for use in cosmetics and that are described in reference books such as the CTFA Cosmetic Ingredient Handbook, Second Edition, The Cosmetic, Toiletries, and Perfume Association, Inc. 1988, 1992. Examples of such optional ingredients are disclosed in U.S. Ser. Nos. 12/361, 634, 10/392,422 filed Mar. 18, 2003; and US Publication 2003/0215522A1, dated Nov. 20, 2003.

Other optional ingredients include organic solvents, especially water miscible solvents and co-solvents useful as solubilizing agents for polymeric structurants and as drying accelerators. Examples of suitable organic solvents are disclosed in U.S. Ser. No. 12/361,634. Other optional ingredients include: latex or emulsion polymers, thickeners such as water soluble polymers, clays, silicas, ethylene glycol distearate, deposition aids, including coacervate forming components. Additional optional ingredients include anti-dandruff actives including but not limited to zinc pyrithione, selenium sulfide and those actives disclosed in US Publication 2003/0215522A1. Further, optional ingredients may comprise cationic surfactants as included above.

In one embodiment, the Articles may encompass the active agents in the form of a physically adsorbed surface resident coating, either as a thin liquid film or as fine particulates. In one embodiment the ratio of the Article to the surface resident coating comprising said at least one active agent is from about 110:1 to about 0.1:1, in another embodiment from about 20:1 to about 0.2:1, and in another embodiment from about 10:1 to about 0.3:1, and in yet another embodiment from about 1:1 to about 0.4:1. The surface resident coating may comprise from about 10% to about 100% active agents by weight of the surface resident coating, in one embodiment from about 30% to about 100%, and in another embodiment from about 50% to about 100%.

The surface resident coating comprising the one or more active agents is located on at least a portion of the surface of the Article and may permeate the Article in whole or in part. Alternatively, the surface resident coating can be included in-between two separate layers of the Article (e.g., sandwiched or encased). The surface resident coating can be sprayed, dusted, sprinkled, coated, surface-printed (e.g., in the shape of a desired adornment, decoration, or pattern), poured on, injected into the interior, dipped, or by any other suitable means, such as by use of a depositor, sifter, or powder bed. Those of skill in the art should understand that the coating can be applied as a powder coating or can be a fluid coating. For instance, where the coating is a fluid coating, the coating can be sprayed, spread, dropped, printed, sandwiched between different articles or different portions of the same article, layered, injected, rolled on, or dipped. The coating can be applied over portions or entire regions of the article's exterior surface, and can be applied in a manner to adorn, decorate, form a logo, design, etc. In one embodiment, the fibrous Articles of encompass one or more water-releasible matrices comprising active agents. The one or more water-releasible matrix complexes comprising active agents may be incorporated into the composition that is manipulated to form the Article. The water-releasible matrix complexes comprising active agents can be incorporated within a surface resident coating. In one embodiment the surface resident coating comprises from about 10% to about 100% of one or more water-releasible matrix complexes comprising active agents, in another embodiment from about 25% to about 100%, and in yet another embodiment from about 40% to about 100%.

The ratio of the water-releasible matrix material to the one or more active agents in the complex is in one embodiment from about 0.5:1 to about 19:1, in another embodiment from about 0.7:1 to about 6:1, and in yet another embodiment from about 1:1 to about 3:1. The water-releasible matrix complexes comprising active agents according to the invention are in particulate form and may have a particle size from about 1 μm to about 200 μm, in another embodiment from about 2 μm to about 100 μm, and in yet another embodiment from about 3 μm to about 50 μm.

The water-releasible matrix materials may include cyclodextrins, as well as high surface area particles that form complexes such as starches, polyethylenes, polyamides, polystyrenes, polyisoprenes, polycarbonates, polyesters, polyacrylates, vinyl polymers polyurethanes, amorphous silica, amorphous silica gel, precipitated silica, fumed silica, aluminosilicates, such as zeolites and alumina, silicates, carbonates, and mixtures thereof. Preferred water-releasible matrix materials include cyclodextrin complexes, silicates, silicas, carbonates, and starch-based materials.

In an additional embodiment, the Articles encompass one or more microcapsules comprising active agents. The one or more microcapsules comprising active agents may be incorporated into the composition that is manipulated to form the Article. The microcapsules comprising active agents can be incorporated within the surface resident coatings. In one embodiment the surface resident coating comprises from about 10% to about 100% of one or more microcapsules comprising active agents, in another embodiment from about 25% to about 100%, and in yet another embodiment from about 40% to about 100%. Unless indicated otherwise, the terms "perfume nanocapsule" and "microcapsule" are within the scope of the term "perfume microcapsule."

The microcapsules may be formed by a variety of procedures that include, but are not limited to, coating, extrusion, spray-drying, interfacial, in-situ and matrix polymerization. The possible shell materials vary widely in their stability toward water. Among the most stable are polyoxymethyleneurea (PMU)-based materials, which may hold certain active agents for even long periods of time in aqueous solution (or product). Suitable microcapsules may include those described in the following references: U.S. Patent Application Nos.: 2003/0125222 A1; 2003/215417 A1; 2003/216488 A1; 2003/158344 A1; 2003/165692 A1; 2004/071742 A1; 2004/071746 A1; 2004/072719 A1; 2004/072720 A1; 2006/0039934 A1; 2003/203829 A1; 2003/195133 A1; 2004/087477 A1; 2004/0106536 A1; and U.S. Pat. Nos. 6,645,479 B1; 6,200,949 B1; 4,882,220; 4,917,920; 4,514,461; 6,106,875 and U.S. Pat. Nos. 4,234,627, 3,594,328 and US RE 32713.

In one embodiment, the Articles may comprise chemical foaming agents. These agents can be processing aid for forming the Articles or enhancing the performance of the active agent in the Articles. The chemical foaming agents may be exothermic (heat released upon foaming) or endothermic (heat absorbed during foaming). The endothermic chemical foaming agent may be useful during fiber formation to absorb heat and foam for providing lower density fibers. Suitable non-limiting examples of endothermic foaming agents include sodium bicarbonate, citric acid and their derivatives, and combinations thereof, which start to evolve gas (mostly carbon dioxide) for foaming around 120° C. Non-limiting examples of exothermic chemical foaming agents include azodicarbonamide (ADC), 4,4'-Oxybis(benzol-sulfonylhydrazide), 5-phenyltetrazole, p-toluylensulfonyl-semicarbazide, p-toluylensulfonyl-hydrazide, and combinations thereof. These exothermic chemical foaming agents become active (evolve mostly nitrogen gas for foaming) at temperatures in excess of 100° C. and release heat (exothermic), which may need to removed by cooling or other means. When used as a processing aid for forming the Articles, the selection of the proper chemical foaming agent is quite dependent on the specific application conditions and requirements, especially processing mixture composition and process conditions and control. It is desirable for the chemical foaming agent to completely decompos and be kept in the processing mixture fluid solution until the fluid blend exits the die or nozzle. Then, the gas should be allowed to expand in the solid phase in the Article. The gas may escape from the Article to form open-celled fibers or may remain trapped. Hydrocerol® (available from Clariant Masterbatches, Holden, Massachussetts, USA), Tracel® (available from Tramaco, Pinneberg, Germany), and OnCap™ (available from PolyOne, Avon Lake, Ohio, USA) are non-limiting examples of commercially available chemical foaming agents. Anti-foaming agents may be added to the Article after the gas from the chemical foaming agents has been released to so that any leftover chemical foaming agent in the Article does not interfere with the performance of the Article, such as during use.

D. Product Form

The Article can be produced in any of a variety of product forms, including Articles used alone or in combination with other consumer product components. The Articles can be used in a continuous or discontinuous manner when used within consumer product compositions.

The Article may be in the form of one or more flat sheets or pads of an adequate size to be able to be handled easily by the user. It may have a square, rectangle or disc shape or any other suitable shape. The pads can also be in the form of a continuous strip including delivered on a tape-like roll dispenser with individual portions dispensed via perforations and or a cutting mechanism. Alternatively, the Articles are in the form of any other shaped object.

The Article may comprise one or more textured, dimpled or otherwise topographically patterned surfaces including letters, logos or figures. The textured Article preferably results from the shape of the Article, in that the outermost surface of the Article contains portions that are raised with respect to other areas of the surface. The raised portions can result from the formed shape of the Article, for example the Article can be formed originally in a dimpled or waffle pattern. The raised portions can also be the result of creping processes, imprinted coatings, embossing patterns, laminating to other layers having raised portions, or the result of the physical form of the Article itself. The texturing can also be the result of laminating the Article to a second Article that is textured.

In a particular embodiment, the Article can be perforated with holes or channels penetrating into or through the Article. These perforations can be formed as part of the web making process via spikes extended from the surface of an adjacent belt, drum, roller or other surface. Alternatively, these perforations can be formed after the web making process via poking or sticking the Articles with pins, needles or other sharp objects. These perforations can be great in number per surface area, but not so great in number so as to sacrifice the integrity or physical appearance of the Article. It has been found that such perforations can increase the dissolution rate of the Articles into water relative to unperforated Articles.

E. Product Types

Non-limiting examples of product type embodiments for use by the Article and methods include personal care articles, oral care articles, personal health care articles, household care articles, and other cleaning articles. Non-limiting examples of the personal care articles include hand cleansing substrates, hair shampoo, hair conditioner, hair color treatment substrates, facial cleansing substrates, body cleansing substrates, shaving preparation substrates, pet care substrates, personal care substrates containing pharmaceutical or other skin care active, moisturizing substrates, sunscreen substrates, chronic skin benefit agent substrates (e.g., vitamin-containing substrates, alpha-hydroxy acid-containing substrates, etc.), deodorizing substrates, anti-acne substrates, skin wrinkle treatment substrates, and combinations thereof. fragrance-containing substrates, and combinations thereof. Non-limiting examples of oral care articles include teeth cleaning articles, teeth whitening articles, tooth care articles, periodontal gum care articles, denture cleaning articles, tongue cleaning articles, breath freshening articles, fluoride containing articles, mouth rinse articles, anti-cavity articles, and combinations thereof. Non-limiting examples of health care articles include pharmaceutical drug containing dosage form articles, over-the-counter drug containing dosage form articles, pro-biotic containing articles, antibacterial substrates, antifungal substrates, anesthetic substrates, wound care substrates, analgesic substrates, antiseptic substrates, anti-inflammatory substrates, and combinations thereof. Non-limiting examples of household care articles include fabric care substrates, dish care substrates, hard surface cleaning substrates, automotive care substrates, fabric fragrance delivery substrates, fabric softener substrates, laundry cleaning substrates, fabric stain removal substrates, fabric anti-wrinkle substrates, fabric static control substrates, fabric on-the-go stain removal substrates, automatic dishwasher cleaning substrates, and so forth.

II. METHOD OF MANUFACTURE

The Article can be prepared by the process comprising: (1) Preparing a processing mixture comprising active agent(s), dissolved polymer structurant(s), plasticizer(s) and other optional ingredients; (2) Fibrillating the processing mixture into fibers by a film fibrillation process comprising a pressurized gas stream directed against a liquid film of the pre-mix to form the fibers and partially drying the fibers by a another or the same pressurized gas stream; (3) Depositing the partially dry fibers on a surface to form a web into a desired one or more shapes to form one or more shaped partially dry Articles; and (4) the optional drying the shaped partially dry Article to a desired final moisture content (e.g., from about 0.5% to about 15% moisture, by addition of energy). Optionally, a surface resident coating can be applied to the Article. The surface resident coating can be applied on the surface of fibers either when the fibers are in flight to the collector before forming a web, or after the web has been dried, as explained later in the Surface Resident Coating section.

A. Preparation of Processing Mixture

The processing mixture is generally prepared by dissolving the polymer structurant in the presence of water, active agent(s), plasticizer and other optional ingredients by heating followed by cooling. This can be accomplished by any suitable heated batch agitation system or via any suitable continuous system involving either single screw or twin screw extrusion or heat exchangers together with either high shear or static mixing. Any process can be envisioned such that the polymer is ultimately dissolved in the presence of water, the active agent(s), the plasticizer, and other optional ingredients including step-wise processing via pre-mix portions of any combination of ingredients.

The processing mixtures can comprise: from about 15% to about 60% solids, in one embodiment from about 20% to about 55% solids, and in another embodiment from about 25% to about 50% solids, by weight of the processing mixture before fiber formation; and have a viscosity of from about 5,000 centipoise to about 150,000 centipoise, in one embodiment from about 10,000 centipoise to about 125,000 centipoise, in another embodiment from about 15,000 centipoise to about 100,000 centipoise, in another embodiment from about 20,000 centipoise to about 75,000 centipoise, and in still another embodiment from about 25,000 centipoise to about 60,000 centipoise.

The % solids content is the summation of the weight percentages by weight of the total processing mixture of all of the solid, semi-solid and liquid components excluding water and any obviously volatile materials such as low boiling alcohols. The processing mixture viscosity values are measured using a TA Instruments AR500 Rheometer with 4.0 cm diameter parallel plate and 1,200 micron gap at a shear rate of 1.0 reciprocal seconds for a period of 30 seconds at 23° C.

B. Forming Fibers from the Processing Mixture

Fibers can be formed from many processes including, but not limited to, meltblowing processes, spunbonding processes, bonded carded web processes, melt fibrillation and electrospinning and combinations thereof. The method of making the fibers can include a single step fibrillation process. Typical single step fibrillation processes used for thermoplastic polymers include melt blowing, melt film fibrillation, spun bonding, melt spinning in a typical spin/draw process, and combinations thereof.

Spunbonded fibers refers to small diameter fibers which are formed by extruding molten thermoplastic material as filaments from a plurality of fine, usually circular capillaries of a spinneret with the diameter of the extruded filaments then being rapidly reduced as described in U.S. Pat. Nos. 3,692,618, 3,802,817, 3,338,992, 3,341,394, 3,502,763, 3,502,538, and 3,542,615.

Meltblown fibers mean fibers formed by extruding a molten thermoplastic material through a plurality of fine, usually circular, die capillaries as molten threads or filaments into converging high velocity gas streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed in U.S. Pat. No. 3,849,241.

Methods to produce fine fibers additionally comprise melt fibrillation and electrospinning Melt fibrillation is a general class of making fibers defined in that one or more polymers are molten and are extruded into many possible configurations (e.g., co-extrusion, homogeneous or bicomponent films or filaments) and then fibrillated or fiberized into filaments. Meltblowing is one such specific method (as described herein). Melt film fibrillation is another method that may be used to produce submicron fibers. A melt film is produced from the melt and then a fluid is used to form fibers from the melt film. Examples of this method comprise U.S. Pat. Nos. 6,315,806, 5,183,670, and 4,536,361, to Torobin et al., and U.S. Pat. Nos. 6,382,526, 6,520,425, and 6,695,992, to Reneker et al. and assigned to the University of Akron. The process according to Torobin uses one or an array of co-annular nozzles to form a fluid film which is fibrillated by high velocity air flowing inside this annular film. Other melt film fibrillation methods and systems are described in the U.S. Pat. Nos. 7,666,343 and 7,931,457 to Johnson, et al., U.S. Pat. No. 7,628,941, to Krause et al., and U.S. Pat. No. 7,722,347, to Krause, et al., and provide uniform and narrow fiber distribution, reduced or minimal fiber defects such as unfiberized polymer melt (generally called "shots"), fly, and dust, for example. These methods and systems further provide uniform nonwoven webs for absorbent hygiene articles.

Electrospinning is a commonly used method of producing sub-micron fibers. In this method, typically, a polymer is dissolved in a solvent and placed in a chamber sealed at one end with a small opening in a necked down portion at the other end. A high voltage potential is then applied between the polymer solution and a collector near the open end of the chamber. The production rates of this process are very slow and fibers are typically produced in small quantities. Another spinning technique for producing sub-micron fibers is solution or flash spinning which utilizes a solvent.

There is a difference between submicron diameter fibers made with electro-spinning versus those made with melt-fibrillation, namely the chemical composition. Electro-spun submicron fibers are made of generally soluble polymers of lower molecular weight than the fibers made by melt-fibrillation. Commercially-viable electro-spinning methods have been described in U.S. Pat. No. 7,585,437, to Jirsak et al., U.S. Pat. No. 6,713,011 to Chu et al., U.S. Pat. Publ. No. 2008/0237934, to Reneker et al, U.S. Pat. Publ. Nos. 2008/0277836 and 2008/0241297, to Park, and U.S. Pat. Publ. No. 2009/0148547, to Petras et al.

In one embodiment, a form of melt film fibrillation process is used. Generally, this process involves providing a thermoplastic polymeric melt, utilizing a pressurized gas stream to impinge on to the polymeric melt to form multiple fine fibers. Suitable melt film fibrillation methods are described in—for example, U.S. Pat. Nos. 4,536,361, 6,315,806, and 5,183,670 to Torobin; U.S. Pat. Nos. 6,382,526, 6,520,425, and 6,695,992, to Reneker; U.S. Pat. No. 7,666,343 to Johnson et al; U.S. Pat. No. 7,628,941, to Krause et al, and U.S. Pat. Publ. No. 2009/0295020, to Krause, et al, published on Dec. 3, 2009—all of which are incorporated herein as reference in their entirety. The melt film fibrillation methods can utilize different processing conditions. Torobin's and Reneker's method more specifically includes the steps of feeding the polymer melt into an annular column and forming a film at the exit of the annular column where a gas jet space is formed. A gas column then provides pressures on the inner circumference of the polymer film. When the polymer melt film exits the gas jet space, it is blown apart into many small fibers, including nanofibers, due to the expanding central gas.

While the melt film fibrillation methods, included as reference above, describe the use of thermoplastic polymer melt, it was surprising and non-intuitive to discover that a film fibrillation method can be used for making fibers of the processing mixture fluids. Specifically, as used, a fluid film fibrillation process comprises a pressurized gas stream flowing within a confined gas passage, comprising an upstream converging wall surfaces and a downstream diverging wall surfaces into which the processing mixture fluid is introduced to provide an extruded processing mixture fluid film on a heated wall surface that is impinged by the gas stream flowing within the gas passage, effective to fibrillate the processing mixture fluid film into fibers. "Converging" means that the cross-sectional area decreases in the direction of gas flow; and "diverging" means that the crosssectional area increases in the direction of gas flow. In one embodiment, the gas passage comprises a first, upstream section into which the gas enters from a supply end, a transition region, and a second, downstream section in which the gas flows to an exit end, wherein the transition region fluidly connects the first section to the second section, and the gas passage ends at the exit end of the second section. In a particular embodiment, the first section of the gas passage has a monotonically decreasing cross-sectional area from the supply end to the transition region, and the second section of the gas passage has a monotonically increasing cross-sectional area from the transition region to the exit end of the second section. At least one flowing processing mixture fluid stream is transmitted through at least one bounded passage which ends in at least one opening in at least one of the opposing heated walls. The processing mixture fluid is heated sufficiently in transit to make and keep it flowable until introduced into the gas passage. Each processing mixture fluid stream extrudes in the form of a film from each opening. Each extruded processing mixture fluid film joins with the gas stream and the processing mixture fluid film is fibrillated to form fibers exiting from the exit end of the second section of the gas passage. For purposes herein, "monotonically decreasing cross-sectional area" means "strictly decreasing cross-sectional area" from the upper inlet) end to the lower end of the upstream nozzle section, and "monotonically increasing cross-sectional area" means "strictly increasing cross-sectional area" from the upper end to the exit end of the downstream section of the nozzle.

In a particular embodiment, each extruded processing mixture fluid film joins with the gas stream in the second section of the gas passage. The introduction of the processing mixture fluid in the second section of the nozzle system on a heated diverging support wall has been found to especially facilitate production of high quality fibers and resulting webs. In a further embodiment, the location where the extruded processing mixture fluid film joins with the gas in the second, downstream section in order to produce the best quality fibers and web depends on the type of gas, the nozzle geometry, including angles and transitions, and the pressure of the gas, and can be located in the upper half of the second section such as for low gas pressure conditions, and can be located in the lower, downstream half of the second section such as for high gas pressure conditions. In a particular embodiment, only one processing mixture fluid film forms on at least one of the heated walls, the gas pressure exceeds about 10 psi, and each processing mixture passage opening from which processing mixture film extrudes is located in a second, downstream half of the second section between the transition region and the exit end of the second section. It has been found that the second half of the downstream second section can provide an optimal gas velocity region where fluid film fibrillation is accomplished very efficiently, yielding higher quality fibrous product.

For the purposes of this disclosure, the bounded passages for pressurized gas and processing mixture fluid together will be referred as "nozzle" or "nozzle system". The nozzle may have bounded passages in a rectangular slot configurations or circular rounded configuration or elongated oval configuration or any configuration that would enable formation of one or more processing mixture fluid film(s) to be impinged by one or more pressurized gas streams. In particular, for a rectangular slot configuration, one or more pressurized gas streams may flow through a bounded rectangular slot passage to impinge on the processing mixture fluid film that forms on a rectangular wall surface to form the processing mixture fibers. In such rectangular slot configuration, the bounded passage for one or more processing mixture fluid may be circular rounded, or elongated oval, or rectangular slot, or any other shape.

Figure 2:
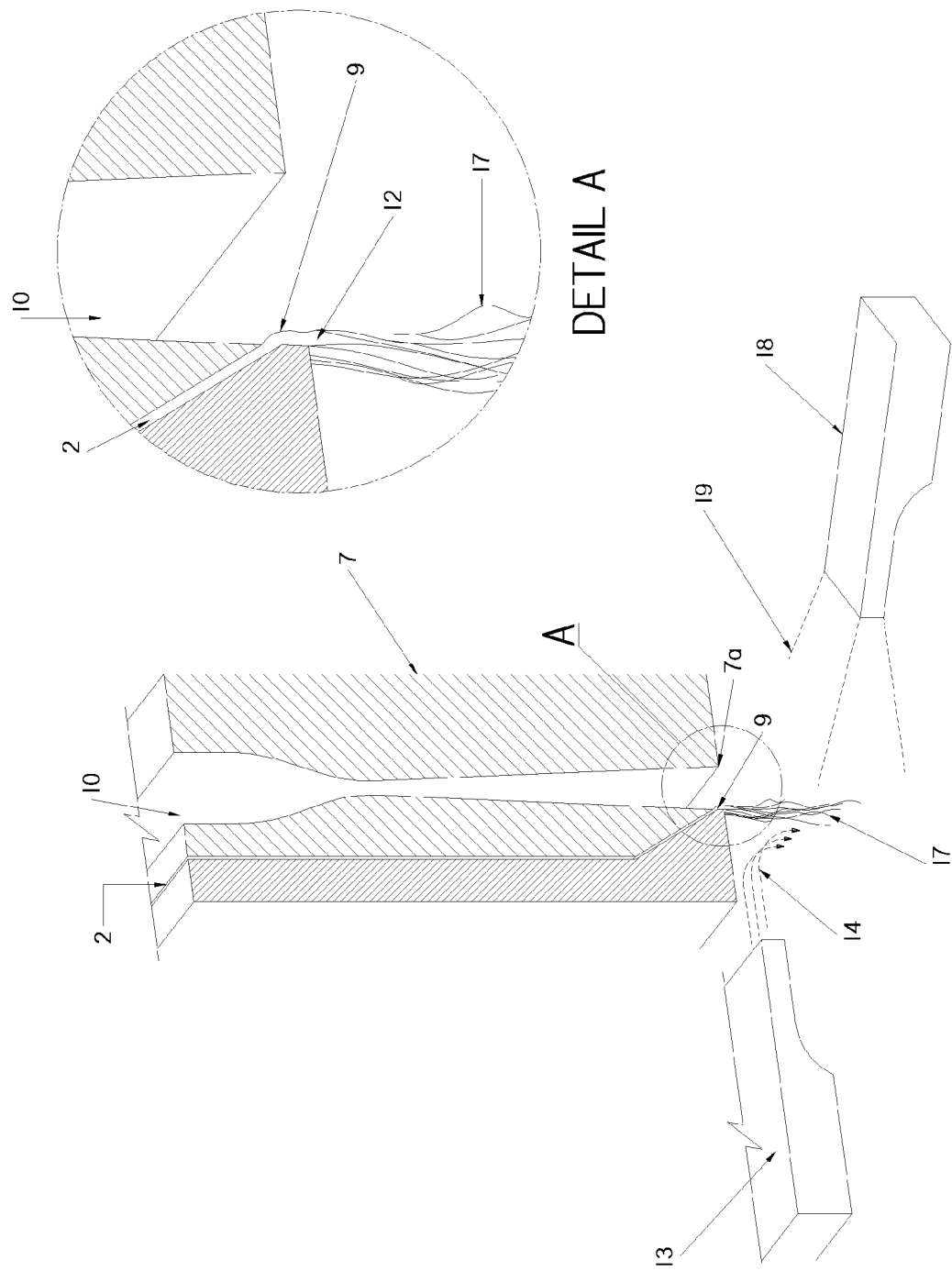
FIG. 2 is a schematic of a slot fluid film fibrillation nozzle for forming fibers of the processing mixture fluid.

An example of a circular rounded nozzle and a slot nozzle for fluid film fibrillation method are further illustrated in FIGS. 1 and 2, respectively. These preferred embodiments illustrate a nozzle 7, 20 with orifice 7a which forms the fibers 17. The process more specifically includes the steps of heating the processing mixture fluid 2 and forming a liquid film 9 across an orifice 7a. The processing mixture fluid will contain the water soluble polymer and any other desired ingredients. The processing mixture fluid 2 is extruded through an orifice 7a, which in turn contains a pressurized gas stream 10 such that the processing mixture fluid 2 extrudes as an elongated film 12. The orifice 7a may be part of a nozzle 7 and the nozzle 7 may be optimized for process stability. A fiberizing fluid stream 10, such as a pressurized gas stream, is blown to form an elongated film 12. The fiberizing fluid stream 10 will then provide pressure on the inner surface (adjoining fiberizing fluid stream) of the elongated film 12. Thinned wall or weakened portions may form in the film 12 to more easily and controllably enable the formation of fibers including nanofibers 17. The weakened portions may result from notches or projections located on the outer surface of the jet 10 or on the inner surface of the processing mixture fluid extrusion orifice 7a. The weakened portions may also result spontaneously due to local surface pressure on the fluid film and/or fluid film flow rate differences across the perimeter of the film. The elongated processing mixture fluid film 12 is then subjected to a fluid to form a multiplicity fibers 17. This fluid can be the pressurized gas stream 10 or an entraining fluid 14 or any fluid stream. The entraining fluid 14 is from transverse jet 13. If advantageous, a nozzle 18 providing cooling or heating fluid 19 to the formed fibers 17 may be used.

The processing mixture 2 is typically heated until it forms a liquid and flows easily. The processing mixture fluid 2 may be at a temperature of from about 0° C. to about 150° C., in one embodiment from about 10° C. to about 120° C., and in another embodiment from about 20° C. to about 100° C. The temperature of the polymer 2 depends on the processing mixture fluid composition. The heated processing mixture fluid 2 is at a pressure from about 15 psia to about 220 psia, or preferably from about 20 psia to about 150 psia, or more preferably from about 25 psia to about 100 psia.

In some cases, the processing mixture fluid film may coalesce immediately after forming. In the case of the coalesced film, it may be preferred to have thinned walls or weakened portions in the film to aid in the fibrillation. Non-limiting examples of the fiberizing fluid are gases such as nitrogen or in another embodiment air or any other fluid compatible (defined as reactive or inert) with processing mixture composition. The fiberizing fluid 10 can be at a temperature close to the temperature of the heated processing mixture fluid 2. The fiberizing fluid 10 temperature may be at a higher temperature than the heated processing mixture fluid 2 to help in the flow of the processing mixture fluid 2 and the formation of the fluid film 9. Alternatively, the fiberizing fluid 10 temperature can be below the heated processing mixture fluid 2 temperature. In one embodiment, the fiberizing fluid temperature is about 100° C. above the heated processing mixture fluid 2, in another embodiment about 50° C. above the heated processing mixture fluid 2, or just at temperature of the heated processing mixture fluid 2. The pressure of the fiberizing fluid 10 is sufficient to fibrillate the processing mixture fluid into fibers 17 and is above the pressure of the heated processing mixture fluid as it is extruded out of the orifice 7a.

The fiberizing fluid 10 may have a velocity of more than about 200 meter per second at the location of film fibrillation. In one embodiment, at the location of film fibrillation, the fiberizing fluid velocity will be more than about 300 meter per second, i.e., transonic velocity; in another embodiment more than about 330 meter per second, i.e., sonic velocity; and in yet another embodiment from about 350 to about 800 meters per second, i.e., supersonic velocity. The fiberizing fluid may pulsate or may be a steady flow.

The processing mixture fluid 2 throughput will primarily depend upon the specific processing mixture fluid used, the nozzle design, and the temperature and pressure of the processing mixture fluid. The processing mixture fluid 2 throughput will be more than about 1 gram per minute per orifice, for example in a circular nozzle illustrated in the FIG. 1. In one embodiment, the processing mixture fluid throughput will be more than about 10 gram per minute per orifice and in another embodiment greater than about 20 gram per minute per orifice, and in yet another embodiment greater than about 30 gram per minute per orifice. In an embodiment with the slot nozzle, such as the one illustrated in the FIG. 2, the processing mixture fluid throughput will be more than about 0.5 kilogram per hour per meter width of the slot nozzle. In another slot nozzle embodiment, the processing mixture fluid throughput will be more than about 5 kilogram per hour per meter width of the slot nozzle, and in another slot nozzle embodiment, the processing mixture fluid throughput will be more than about 10 kilogram per hour per meter width of the slot nozzle, and in yet another slot nozzle embodiment, the processing mixture fluid throughput will be more than about 20 kilogram per hour per meter width of the slot nozzle. In certain embodiments of the slot nozzle, the processing mixture fluid throughput may exceed about 40 kilogram per hour per meter width of the slot nozzle. There will likely be several orifices 7a operating at one time which further increases the total production throughput. The throughput, along with pressure, temperature, and velocity, are measured at the die orifice exit for circular 7a and slot nozzles 20.

The fibrillation of the fibers may occur before the fibers and fluid exit the orifice. Once the elongated film exits the orifice, the fibers are formed. Commonly, the formation of fibers occurs immediately upon exiting the orifice. One or more fluid streams may be used to form the multiplicity of fibers. The pressurized gas or fluid stream 10 can be the fluid stream adjoining the processing mixture fluid film, an entraining fluid, or any other fluid stream. Optionally, an entraining fluid 14 can be used to induce a pulsating or fluctuating pressure field to help in forming a multiplicity of fibers 17. Non-limiting examples of the entraining fluid 14 are pressurized gas stream such as compressed air, nitrogen, oxygen, super-heated steam, or any other fluid compatible (defined as reactive or inert) with the processing mixture composition. As shown in FIGS. 1 and 2, the entraining fluid 14 may be provided by a transverse jet 13 which is located to direct the flow of entraining fluid 14 over and around the film 12 and fiber 17 forming region. The entraining fluid 14 can have a low velocity or a high velocity, such as an near sonic or super sonic speeds. An entraining fluid with a low velocity will typically have a velocity of from about 1 to about 100 meter per second and in one embodiment from about 3 to about 50 meter per second. It is desirable to have low turbulence in the entraining fluid stream 14 to minimize fiber-to-fiber entanglements, which usually occur due to high turbulence present in the fluid stream. The temperature of the entraining fluid 14 can be the same as the above fiberizing fluid 10, or a higher temperature to aid drying of fibers, and ranges from about 80° C. to 300° C. and typically from about 100° C. to about 250° C. The moisture content or the relative humidity of the entraining fluid 14 when used as drying fluid is very low, generally less than 20%, in another embodiment less than 10%, in another embodiment less than 5%, and in yet another embodiment less than 1%.

Optionally, an additional fluid stream, heating or drying fluid 19, can also be used. The additional fluid stream 19 may be a pressurized gas stream such as compressed air, nitrogen, oxygen, super-heated steam, or any other fluid compatible (defined as reactive or inert) with the processing mixture composition. This additional fluid stream 19 is located to direct fluid into the fibers 17 to dry the fibers. It is desirable to have low turbulence in the entraining fluid stream 19 to minimize fiber-to-fiber entanglements, which usually occur due to high turbulence present in the fluid stream. If the additional fluid is used as a heating or drying fluid, it is at a temperature of from about 80° C. to 300° C. and typically from about 100° C. to about 250° C. The moisture content or the relative humidity of the additional fluid stream when used as drying fluid is very low, generally less than 20%, in one embodiment less than 10%, in yet another embodimentless than 5%, and in yet another embodiment less than 1%. The additional fluid stream 19 may form a "curtain" or "shroud" around the fibers of the processing mixture exiting from the nozzle. Suitable examples of such "curtain" or "shroud" are disclosed in the U.S. Pat. No. 7,628,941 to Krause, et al and U.S. Pat. Nos. 6,382,526 and 6,695,992 to Reneker, respectively, which all are incorporated herein as reference in their entirety. Any fluid stream may contribute to the fiberization of the processing mixture fluid and can thus generally be called fiberizing fluids.

The fibers of the processing mixture may be partially or completely dried in flight to the collector by any or combination of the fiberizing fluids—the fiberizing fluid pressurized gas stream 10, the entraining fluid 14, or the additional fluid stream 19. Alternatively, the fiberizing fluid pressurized gas stream 10 or the first pressurized gas stream may be the only fluid stream used for fibrillation and partially or completely drying the processing mixture fibers. In such instance, the drying fluid stream is continuation of the first fluid stream 10. Alternatively, the first fiberizing fluid stream 10 and the second entraining fluid stream 14 may the fluid streams used for fiberizing and drying, respectively. Alternatively, the first fiberizing fluid stream 10 and the second additional fluid stream 19 may the fluid streams used for fiberizing and drying, respectively. In a particular embodiment, the drying additional fluid stream 19 may be adjacent to the first fiberizing fluid stream 10. In another embodiment the drying additional fluid stream 19 may be at an angle to the first fiberizing fluid stream 10 after exiting the nozzle. The angle of the drying additional fluid stream 19 may range from about 0° (parallel) to 90° (perpendicular) to the first fiberizing fluid stream 10 as it exits the nozzle. The fluid stream 19 can have a low velocity or a high velocity, such as a near sonic or super sonic speeds. The additional fluid stream with a low velocity will typically have a velocity of from about 1 to about 100 meter per second and in one embodiment from about 3 to about 50 meter per second. One or more drying fluid stream(s) at least partially dry the in-flight fibers fibrillated from the processing mixture film. In a particular embodiment, one or more drying fluid stream(s) may dry the fibers to desired moisture content of the Article from about 0.5% to about 15% moisture. The temperature and moisture content of one or more drying fluid stream(s) may be optimized to dry the fibers to the desired moisture content by one ordinary skilled in the art of dry spinning.

After the processing fixture fluid film is formed, the film or the fibers may alternatively be subject to an additional process that promotes the formation of micro and nanofibers with diameter less than about 1 micrometer. The further processing would occur immediately after formation of the elongated film. The additional processing can utilize one or more Laval nozzles to speed up the gas velocities to sonic and/or supersonic range. When processing mixture is exposed to such high gas velocities, it bursts into multiplicity of fine fibers. Examples of a Laval nozzle are described in Nyssen et al., U.S. Pat. No. 5,075,161 (included herein as a reference in its entirety), in which a method of bursting polyphenylene sulfide melt into fine filaments is disclosed. The Laval nozzle may be positioned just after the nozzle when the elongated processing mixture film is produced. Alternatively, Laval nozzle could be positioned just after the fibers have formed to further reduce the fiber size. The fibers can be produced by subjecting the processing mixture streams to drawing out and extruding them into a gaseous medium which flows essentially parallel to the processing mixture streams and attains sonic or supersonic speed. This simultaneous deformation and cooling gives rise to fine or extremely fine fibers of finite length. The spinning speed, temperature, and the position of the Laval nozzle are appropriately set to achieve desired fineness and drying of fibers.

Various processes and combination of processes can be used to make the webs of the described herein. Fiber bursting, as disclosed in U.S. Pat. No. 7,326,663 by Sodemann et al. can be combined with fluid film fibrillation described herein on two separate beams on a single line. Various aspects of fiber bursting can be incorporated into fluid film fibrillation, such as producing fibers of different strengths and diameters to provide a desired combination of properties. Alternatively, aspects of fluid film fibrillation can be included in other fibrillation processes to increase the throughput rate by utilizing a fluid film fibrillation to form fibers. For example, the fluid film fibrillation process described herein could be modified to include a Laval nozzle to aid in drawing down the fibers. Drawing down can aid in further attenuation of the fibers.

The fibers described herein may also be produced by other spinning methods that typically yield submicron fibers. Such methods include electrospinning, electroblowing, and flash spinning. In general, electrospinning employs an electrostatic force to draw a charged liquid polymeric formulation from a source to a collector. An electrostatic field is used to accelerate the liquid formulation from the source to the collector on which the fibers are collected. Suitable and non-limiting examples of electrospinning methods for making fibers as described herein, have been described in U.S. Pat. No. 7,585,437, to Jirsak et al., U.S. Pat. No. 6,713,011 to Chu et al., U.S. Pat. Publ. No. 2008/0237934, to Reneker et al, U.S. Pat. Publ. Nos. 2008/0277836 and 2008/0241297, to Park, U.S. Pat. Publ. No. 2009/0148547, to Petras et al, and U.S. Pat. Publ. No. 2006/0264130, to Karles, et al.

The electroblowing method comprises feeding a polymeric solution to a spinning nozzle to which a high voltage is applied while compressed gas is used to envelop the polymer solution in a forwarding gas stream as it exits the nozzle, and collecting the resulting nanofiber web on a grounded suction collector. Suitable and non-limiting examples of electroblowing methods, included herein as references in their entirety, comprise U.S. Pat. No. 7,582,247 to Armantrout et al, U.S. Pat. No. 7,585,451 to Bryner et al, U.S. Pat. No. 7,618,579 to Kim et al, U.S. Pat. Publ. No. 2006/0097431 to Hovanec, U.S. Pat. Publ. No. 2006/0012084 to Armantrout et al, and U.S. Pat. Publ. No. 2005/0073075 to Chu et al.

Another process to make fibers of the described herein is flash spinning, described in U.S. Pat. No. 3,081,519 to Blades and White (non-limiting example). In the flash spinning process, a polymeric solution at a temperature above the boiling point of the solvent and at a pressure at least autogenous is extruded into a medium of lower temperature and substantially lower pressure. The sudden boiling which occurs at this point causes either microcellular structures or fibrillated networks to form. The fibrillated materials tend to be formed when the pressure changes are most severe, or when more dilute solutions are used. Under these circumstances the vaporizing liquid within the extrudate forms bubbles, breaks through confining walls, and cools the extrudate, causing solid polymer to form therefrom. The resulting multifibrous strand has an internal fine structure or morphology characterized as a three-dimensional integral plexus consisting of a multitude of essentially longitudinally extended, interconnecting, random-length, fibrous elements, referred to as film-fibrils. These film-fibrils have the form of thin ribbons of a thickness, typically, less than 4 micrometer. Other suitable and non-limiting examples of the flash spinning process, included herein as references in their entirety, comprise U.S. Pat. Nos. 5,977,237 and 5,250,237 to Shin et al, U.S. Pat. No. 5,788,993 to Bryner et al, U.S. Pat. No. 6,638,470 to Schweiger, U.S. Pat. No. 4,260,565 to D'Amico et al, and U.S. Pat. No. 7,118,698 to Armantrout et al.

In a particular embodiment, the processing mixture may be spun into submicron (diameter less than about 1 micrometer) or micro-fiber (diameter ranging from about 1 micrometer to about 10 micrometer) using methods selected from the group of fluid film fibrillation, melt fibrillation, electrospinning, electroblowing, flash spinning, or combinations thereof.

The above methods, such as fluid film fibrillation, fiber bursting, electrospinning, or electroblowing, produce a significant number of dissolvable fibers with an average diameter less than about 1 micrometer, or sub-micron fibers. In an embodiment, the article comprising Article may have at least 25% of all the dissolvable fibers with an average diameter less than about 1 micrometer, in one embodiment at least 35% of all the dissolvable fibers with an average diameter less than about 1 micrometer, in another embodiment at least 50% of all the dissolvable fibers with an average diameter less than about 1 micrometer, and in yet another embodiment at least 75% of all the dissolvable fibers with an average diameter less than about 1 micrometer. However, it may be desirable for a particular Article produced by the methods of described herein be such that the methods are optimized to produce a significant number of dissolvable fibers with an average diameter less than about 150 micrometer, in one embodiment less than about 100 micrometer, in another embodiment less than about 10 micrometer, and yet another embodiment less than about 1 micrometer with a relative standard deviation of less than 100%, alternatively less than 80%, alternatively less than 60%, alternatively less than 50%, such as in the range of 10% to 50%, for example. As mentioned earlier in the present disclosure, the significant number means at least 10% of all the dissolvable fibers, in one embodiment at least 25% of all the dissolvable fibers, in another embodiment at least 50% of all the dissolvable fibers, yet another embodiment at least 75% of all the dissolvable fibers.

C. Forming the Fibrous Web Structure

The partially dry or dried to desired moisture content fibers of the processing mixture are laid down on a collector to form a web. The collector is typically a conveyor belt or a drum. The collector can be porous and vacuum may be applied to provide suction to aid fiber lay down on the collector. The distance from the orifice to the collector distance, commonly called die-to-collector distance (DCD), can be optimized for desired web properties. It may be desired to utilize more than one DCD used in a web, to change the DCD during production, or to have different beams with different DCDs. It may be desirable to form a web with different uniformities by changing the DCD. If the DCD is such that fibers are not sufficiently dried before depositing on the collector, the wet or insufficiently dry fibers may coalesce to form blobs or bundles that may not be desirable and would constitute as defects. Alternatively, it may be desirable for an Article to have some or all fibers coalesce completely or partially, e.g., to have structural integrity. If the DCD is large and such that fibers are sufficiently dried, the fibers may entangle or stick to one another, but not coalesce, to form bundles or ropes that may not be desirable. Therefore, depending on the desired Article, the DCD may be set to form fibrous web with desirable uniformity and sufficient dryness. Alternatively, the webs of desirable uniformity may be further dried to obtain moisture content desired in the Article.

Additionally, the die-to-collector distance may be altered along with the vacuum underneath the collector to obtain desired density of the web. Generally, the shorter DCD and/or higher vacuum provides denser webs relative to the larger DCD. At shorter DCD and/or higher vacuum, the fibers tend to be "forced" together tightly by the fiberizing fluid jet and/or vacuum suction, while at the larger DCD and/or lower vacuum, the fibers stay fluffy and thus lower density. Therefore, depending on the desired Article density, it may be desirable to optimize DCD and/or vacuum for uniformity, dryness, and density.

The fibrous webs of the processing mixture may be formed a desired shape or shapes including, but not limited to (i) depositing the fibrous web to specially designed molds comprising a non-interacting and non-stick surface including Teflon, metal, HDPE, polycarbonate, neoprene, rubber, LDPE, glass and the like; (ii) depositing the fibrous web into cavities imprinted in dry granular starch contained in a shallow tray, otherwise known as starch moulding forming technique; and (iii) depositing the fibrous web onto a continuous belt or screen comprising any non-interacting or non-stick material Teflon, metal, HDPE, polycarbonate, neoprene, rubber, LDPE, glass and the like which may be later stamped, cut, embossed or stored on a roll.

D. The Optional Drying the Fibrous Web of the Processing Mixture

The optional drying of the formed partially dried fibrous web of the processing mixture may be accomplished by any suitable means including, but not limited to (a) multi-stage inline dryers using convection or through-air drying; (b) super-heated steam dryers; (c) drying room(s) including rooms with controlled temperature and pressure or atmospheric conditions; (d) ovens including non-convection or convection ovens with controlled temperature and optionally humidity; (e) truck/tray dryers, impingement ovens; (f) rotary ovens/dryers; (g) inline roasters; (h) rapid high heat transfer ovens and dryers; (i) dual plenum roasters, and (j) conveyor dryers.

Optional ingredients may be imparted during any of the above described four processing steps or even after the drying process.

E. The Optional Preparing the Surface Resident Coating Comprising the Active Agent The preparation of the surface resident coating comprising the active agent may include any suitable mechanical, chemical, or otherwise means to produce a particulate composition comprising the active agent(s) including any optional materials as described herein, or a coating from a fluid.

Optionally, the surface resident coating may comprise a water releasable matrix complex comprising active agent(s). In one embodiment, the water releasable matrix complexes comprising active agent(s) are prepared by spray drying wherein the active agent(s) is dispersed or emulsified within an aqueous composition comprising the dissolved matrix material under high shear (with optional emulsifying agents) and spray dried into a fine powder. The optional emulsifying agents can include gum arabic, specially modified starches, or other tensides as taught in the spray drying art (See Flavor Encapsulation, edited by Sara J. Risch and Gary A. Reineccius, pages 9, 45-54 (1988), which is incorporated herein by reference). Other known methods of manufacturing the water releasable matrix complexes comprising active agent(s) may include but are not limited to, fluid bed agglomeration, extrusion, cooling/crystallisation methods and the use of phase transfer catalysts to promote interfacial polymerisation. Alternatively, the active agent(s) can be adsorbed or absorbed into or combined with a water releasable matrix material that has been previously produced via a variety of mechanical mixing means (spray drying, paddle mixers, grinding, milling etc.). In one embodiment, the water releasable matrix material in either pellet or granular or other solid-based form (and comprising any minor impurities as supplied by the supplier including residual solvents and plasticizers) may be ground or milled into a fine powder in the presence of the active agent(s) via a variety of mechanical means, for instance in a grinder or hammer mill.

Where the article has a particulate coating, the particle size is known to have a direct effect on the potential reactive surface area of the active agents and thereby has a substantial effect on how fast the active agent delivers the intended beneficial effect upon dilution with water. In this sense, the active agents with smaller particle sizes tend to give a faster and shorter lived effect, whereas the active agents with larger particle sizes tend to give a slower and longer lived effect. In one embodiment the surface resident coatings may have a particle size from about 1 µm to about 200 µm, in another embodiment from about 2 µm to about 100 µm, and in yet another embodiment from about 3 µm to about 50 µm.

In some embodiments, it is helpful to include inert fillers within the grinding process, for instance aluminum starch octenylsuccinate under the trade name DRY-FLO® PC and available from Akzo Nobel, at a level sufficient to improve the flow properties of the powder and to mitigate inter-particle sticking or agglomeration during powder production or handling. Other optional excipients or cosmetic actives, as described herein, can be incorporated during or after the powder preparation process, e.g., grinding, milling, blending, spray drying, etc. The resulting powder may also be blended with other inert powders, either of inert materials or other powder-active complexes, and including water absorbing powders as described herein.

In one embodiment, the active agents may be surface coated with non-hygroscopic solvents, anhydrous oils, and/or waxes as defined herein. This may include the steps of: (i) coating the water sensitive powder with the non-hydroscopic solvents, anhydrous oils, and/or waxes; (ii) reduction of the particle size of the active agent particulates, prior to, during, or after a coating is applied, by known mechanical means to a predetermined size or selected distribution of sizes; and (iii) blending the resulting coated particulates with other optional ingredients in particulate form. Alternatively, the coating of the non-hydroscopic solvents, anhydrous oils and/or waxes may be simultaneously applied to the other optional ingredients, in addition to the active agents, of the surface resident coating composition and with subsequent particle size reduction as per the procedure described above.

Where the coating is applied to the substrate as a fluid (such as by as a spray, a gel, or a cream coating), the fluid can be prepared prior to application onto the substrate or the fluid ingredients can be separately applied onto the substrate such as by two or more spray feed steams spraying separate components of the fluid onto the substrate.

F. The Optional Combining of the Surface Resident Coating Comprising the Active Agents with the Article Any suitable application method can be used to apply the surface resident coating comprising active agent to the personal care article such that it forms a part of the personal care article. For instance, the Article can have a tacky surface by drying the Article's surface to a specific water content before application of powder to facilitate the adherence of the surface resident coating comprising the active agents to the Article. In one embodiment, the Article is dried to a moisture content of from about 0.1% to about 25%, in one embodiment from about 3% to about 25%, in another embodiment from about 5% to about 20% and in yet another embodiment from about 7% to about 15%. Alternatively, a previously dried Article's surface can be made to reversibly absorb a desired level of atmospheric moisture prior to application of the powder within a controlled humidity environment for a specific period of time until equilibrium is achieved. In one embodiment, the humidity environment is controlled from about 20% to about 85% relative humidity; in another embodiment, from about 30% to about 75% relative humidity; and in yet another embodiment, from about 40% to about 60% relative humidity.

In another embodiment, the Article is placed in a bag, tray, belt, or drum containing or otherwise exposed to the powder and agitated, rolled, brushed, vibrated or shaken to apply and distribute the powder, either in a batch or continuous production manner Other powder application methods may include powder sifters, electrostatic coating, tribo charging, fluidized beds, powder coating guns, corona guns, tumblers, electrostatic fluidized beds, electrostatic magnetic brushes, and/or powder spray booths. The surface resident coating comprising the active agent can be applied over portions or entire regions of the Article's exterior surface, and can be applied in a manner to adorn, decorate, form a logo, design, etc.

The surface resident coating comprising active agents can be directly applied to fibers as they are being formed. Referring to FIGS. 1 and 2, the surface resident coating may be included in any of the pressurized gas streams 10, 14, or 19, or any additional pressurized gas stream added to the nozzle system. The surface resident coating may adhere and/or get embedded on the surface of partially or desirably dried fibers. Suitable and non-limiting examples of applying surface resident coatings on fibers, included as references herein in their entirety, comprise U.S. Pat. Nos. 7,291,300 and 7,267,789 to Chhabra and Isele, and U.S. Pat. Nos. 6,494,974 and 6,319,342 to Riddell.

Where the coating is applied to the substrate in a fluid, it is preferable that if water is present in the fluid that the water is not sufficient to cause the substrate to undesirable dissolve. In preferred embodiments, the active agent(s) to be applied as an adsorbed thin coating is an anhydrous or substantially anhydrous oil. Other non-water solvents, such as organic solvents which do not cause the substrate to dissolve may also be used. Any suitable application method can be used to apply the active agent(s) in liquid form to the article such that it forms a surface-resident coating that is adsorbed to at least a portion of the solid/air interface of the article as a thin film. For instance, it can be sprayed, spread, dropped, printed, sandwiched between different articles or different portions of the same article, layered, injected, rolled on, or dipped. The active agent(s) can be applied over portions or entire regions of the article's exterior surface, and can be applied in a manner to adorn, decorate, form a logo, design, etc.

To obtain the desired fibrous structure, the methods described herein may be combined. In an embodiment, the dissolvable fibers produced from one or more methods described herein may be mixed homogenously or in a layers to have desired performance for the Articles described herein. Different methods described herein may be optimized to produce dissolvable fibers with substantially or otherwise different actives or use of a particular surfactant, extensional rheology modifier, plasticizer, polymer structurant water soluble polymer, or other optional or required ingredients. Still alternatively, different methods may be optimized to produce dissolvable fibers with different dissolution rates and/or different diameter. In a particular embodiment, the submicron dissolvable fibers produced by the fluid film fibrillation method may be mixed homogenously or in layers with the dissolvable fibers produced from fiber bursting or electrospinning or electroblowing method. In some embodiments, the dissolvable fibrous web structure produced by one or more methods or may be even by the same method of may have a mixture of fibers that have substantially or marginally different fiber diameter distributions, compositions, surface resident coatings, dissolution rates, or combinations thereof. In case of an embodiment with a mixture of fibers that have significantly different fiber diameter distributions, the average diameter of fibers from the different fiber diameter distributions may range from about 0.1 micrometer to about 150 micrometer.

Homogenous mixture of fibers produced by one or more methods may have a performance advantage in optimizing, such as slowing or speeding up the dissolution rates for a particular embodiment Article, e.g., for controlled or timed release of actives. The layering of fibers produced by one or more methods may have a performance advantage in varying the dissolution rate during the use of the Article, for example, certain actives or ingredients of the composition may need to be delivered at different times during the usage of the Article, such as timed release of surfactant and conditioner, or detergent and bleach, or detergent and softener, and so forth. Other advantages of mixing dissolvable fibers produced by the methods described herein may be specific to a particular Article.

The homogenous mixing of fibers may be achieved during the forming of fibrous web structure, such as via use of different nozzles or blocks or beams of nozzles employing different methods in a simulataneous fashion, for example, nozzles arranged in a staggered configuration in two-(planar) and/or three dimensions, or simply dissolvable fiber streams coming in at various angles with fibers depositing onto the collector. Examples of homogenously mixing fibers using an array of plurality of fiber-producing nozzles employing fluid film fibrillation process are provided by Torobin in U.S. Pat. Nos. 6,183,670 and 6,315,806, which are included herein by reference in their entirety. The layering of fibers may be achieved during the forming of the fibrous web structure, such as nozzles of different methods arranged adjacent to one another or following one another separated by a particular distance along the machine direction (the direction conveyor belt is moving) in a continuous manner, for example, nozzles in separate blocks or beams that are arranged in line along the machine direction. Alternatively, the dissolvable fibrous web structures produced by different methods may be combined offline in batches by layering over another before or after drying to desired moisture content. When combined as layers, one or more dissolvable fibrous web structures, produced by one or more methods, may have fibers that are substantially different in different layers of the dissolvable fibrous webs. The difference in fibers may be in substantially or marginally different diameter distributions, compositions, surface resident coatings, dissolution rates, porosities, or combinations thereof. For example, the substantially different fiber diameter distribution of fibers in different layers may have average diameters ranging from about 0.1 micrometer to about 150 micrometer.

The Article may comprise one or more dissolvable fibrous web structures combined (e.g., laminated, layered, sandwiched, embedded, and so forth) with one or more other types of web structures and/or Articles as described in the Background section above. Suitable and non-limiting examples of Articles that may be combined include U.S. Pat. Publ. No. 2004/0048759 to Ribble et al, U.S. Pat. No. 6,106,849 to Malkan et al, U.S. Pat. Publ. No. 2007/0225388 to Cooper et al, U.S. Pat. No. 5,457,895 to Kearney et al, U.S. Pat. Publ. No. 2009/0232873 to Glenn et al, U.S. Pat. No. 7,196,026 and PCT Appl. No. WO2001/47567 to Di Luccio et al, PCT Application No. WO2007/093558 to Simon et al, U.S. Pat. App. Publication Nos. 2008/0035174, 2008/0269095, 2007/0128256, and 2007/0134304 to Auburn-Sonneville et al, U.S. Pat. App. Publication No. 2006/0159730 to Simon, and U.S. Pat. Nos. 5,342,335 and 5,445,785 to Rhim

III. PHYSICAL CHARACTERISTICS

A. Dissolution Rate

The Article has a Dissolution Rate that allows the Article to rapidly disintegrate during use application with water. The Dissolution Rate of the Article is determined in accordance with the two methodologies described below.

Conductivity Dissolution Method: In a 250 ml beaker, 150+/−0.5 grams of distilled water is weighed at room temperature. The beaker is placed on an orbital shaker, for example a VWR model DS-500E and started at 150 RPM. A conductivity probe, for example a VWR model 2052 connected to a VWR conductivity meter, is submerged just below the surface of the water in such a manner that the conductivity probe remains stationary in relation to the motion of the beaker and never touches the side of the beaker. A 0.20+/−0.01 grams of the Article is weighed and placed into the water. Conductivity data is recorded every 15 seconds for 6 minutes, and then once a minute until 30 minutes. The final value is recorded when the conductivity values stopped changing or 30 minutes is reached, whichever is earlier. The conductivity dissolution time is taken as the time it takes in seconds until the conductivity values stop changing or as the maximum of 30 minutes, which ever happens first.

The Article has a conductivity dissolution time of from about 100 seconds to about 1,200 seconds, in another embodiment from about 110 seconds to about 900 seconds, in yet another embodiment from about 120 seconds to about 600 seconds, and in still another embodiment from about 130 seconds to about 300 seconds.

Hand Dissolution Method: 0.5 g of the Article is placed in the palm of the hand while wearing nitrile gloves. 7.5 cm$^3$ of luke warm tap water (from about 30° C. to about 35° C.) is quickly applied to the product via syringe. Using a circular motion, palms of hands are rubbed together 2 strokes at a time until dissolution occurs (up to 30 strokes). Undissolved material (after 30 strokes) is placed in pre-weighed weigh boat. Dry weight of undissolved material is measure the following day. The hand dissolution value is reported as the number of strokes it takes for complete dissolution or as 30 strokes as the maximum.

The Article has a hand dissolution value of from about 1 to about 30 strokes, in one embodiment from about 2 to about 25 strokes, in another embodiment from about 3 to about 20 strokes, and in still another embodiment from about 4 to about 15 strokes.

B. Lather Volume

The Article provides a lather profile as described hereafter. The lather volume assessment is performed on 15 g/10 inch flat Oriental virgin hair switches that have been treated with 0.098 g of artificial liquid sebum [10-22% olive oil, 18-20% coconut oil, 18-20% oleic acid, 5-9% lanolin, 5-9% squalene, 3-6% palmitic acid, 3-6% paraffin oil, 3-6% dodecane, 1-4% stearic acid, 1-4% cholesterol, 1-4% coconut fatty acid, 18-20% choleth-24]. The hair switch is rinsed with 9-11 grain, 100° F. water at 1.5 gallons/min for 20 seconds with a shower nozzle. For testing the liquid control products, 0.75 cm$^3$ of liquid product are applied to the center of the switch, the lower portion of hair on the switch is then rubbed over the product on the hair 10 times in a circular motion, followed by 40 strokes back and forth (a total of 80 strokes). Lather speed is recorded as the number of strokes when the first lather is obviously generated during the 80 strokes. Lather from operator's gloves is transferred to a graduated cylinder with a 3.5 cm inside diameter and with total capacities of either 70 ml, 110 ml, or 140 ml depending on the total amount of lather generated (height modification of standard sized graduated cylinders via a glass shop). Lather from hair is gathered using one downward stroke on the switch with a tight grip and is also placed into the cylinder. Total lather volume is recorded in milliliters. Three runs per test sample are performed and the mean of the three values is calculated. When testing the Article, 0.20+/−0.01 grams of product are weighed with the aid of scissors if required and applied to the switch and then 2 cm$^3$ of additional water are added to the product via syringe. The lathering technique is then performed as described for liquid products after a 10 second waiting time.

C. Fiber Diameter

The diameter of dissolvable fibers in a sample of a web is determined by using a Scanning Electron Microscope (SEM) or an Optical Microscope and an image analysis software. A magnification of 200 to 10,000 times is chosen such that the fibers are suitably enlarged for measurement. When using the SEM, the samples are sputtered with gold or a palladium compound to avoid electric charging and vibrations of the fibers in the electron beam. A manual procedure for determining the fiber diameters is used from the image (on monitor screen) taken with the SEM or the optical microscope. Using a mouse and a cursor tool, the edge of a randomly selected fiber is sought and then measured across its width (i.e., perpendicular to fiber direction at that point) to the other edge of the fiber. A scaled and calibrated image analysis tool provides the scaling to get actual reading in micrometers (µm). Several fibers are thus randomly selected across the sample of the web using the SEM or the optical microscope. At least two specimens from the web (or web inside a product) are cut and tested in this manner. Altogether at least 100 such measurements are made and then all data are recorded for statistic analysis. The recorded data are used to calculate average (mean) of the fiber diameters, standard deviation of the fiber diameters, and median of the fiber diameters. Another useful statistic is the calculation of the amount of the population of fibers that is below a certain upper limit. To determine this statistic, the software is programmed to count how many results of the fiber diameters are below an upper limit and that count (divided by total number of data and multiplied by 100%) is reported in percent as percent below the upper limit, such as percent below 1 micrometer diameter or %-submicron, for example. We denote the measured diameter (in microns) of an individual circular fiber as $d_i$.

In case the fibers have non-circular cross-sections, the measurement of the fiber diameter is determined as and set equal to the hydraulic diameter which is four times the cross-sectional area of the fiber divided by the perimeter of the cross of the fiber (outer perimeter in case of hollow fibers). The number-average diameter, alternatively average diameter is calculated as, $$d_{num} = \frac{\sum_{i=1}^{n} d_i}{n}$$

IV. METHODS OF USE

The compositions described herein may be used for treating hair, hair follicles, skin, teeth, the oral cavity, fabric and hard surfaces. The method for treating these consumer substrates may comprise the steps of: a) applying an effective amount of the Article to the hand, b) wetting the Article with water to dissolve the solid, c) applying the dissolved material to either the target consumer substrate such as to treat, and d) rinsing the diluted treatment composition from consumer substrate. These steps can be repeated as many times as desired to achieve the desired cleansing and or treatment benefit. Alternatively, the Article can be inserted into a machine (such as a washing machine or dish washer) in a unit dose manner and the machine can perform the dissolution, treating and rinsing steps.

According to yet another embodiment, a method is provided for providing a benefit to hair, hair follicles, skin, teeth, the oral cavity, fabric and hard surfaces, comprising the step of applying a composition according to the first embodiment to these target consumer substrates in need of regulating.

Described herein is a method for regulating the condition of hair, hair follicles, skin, teeth, the oral cavity, fabric and hard surfaces, comprising the step of applying one or more compositions described herein to these target consumer substrates in need of regulation.

The amount of the composition applied, the frequency of application and the period of use will vary widely depending upon the purpose of application, the level of components of a given composition and the level of regulation desired. For example, when the composition is applied for whole body or hair treatment, effective amounts generally range from about 0.5 grams to about 10 grams, in one embodiment from about 1.0 grams to about 5 grams, and in another embodiment from about 1.5 grams to about 3 grams.

V. ARTICLE OF COMMERCE

Described herein is an article of commerce comprising one or more compositions described herein, and a communication directing a consumer to dissolve the Article and apply the dissolved mixture to hair, hair follicles, skin, teeth, the oral cavity, fabric and hard surfaces to produce a cleansing effect, a benefit to the target consumer substrate, a rapidly lathering foam, a rapidly rinsing foam, a clean rinsing foam, and combinations thereof. The communication may be printed material attached directly or indirectly to packaging that contains the composition or on the composition itself. Alternatively, the communication may be an electronic or a broadcast message that is associated with the article of manufacture. Alternatively, the communication may describe at least one possible use, capability, distinguishing feature and/or property of the article of manufacture.

VI. EXAMPLES

The following examples further describe and demonstrate embodiments described herein.

The examples are given solely for the purpose of illustration and are not to be construed as limitations, as many variations thereof are possible without departing from the spirit and scope of the invention. All exemplified amounts are concentrations by weight of the total composition, i.e., wt/wt percentages, unless otherwise specified.

Example 1: Preparation of Shampoo or Body Wash Article Via a Spunbond Process The following surfactant/polymer liquid processing composition is prepared at the indicated weight percentages as described in Table 1 below.

TABLE 1

| Component | |
|---|---|
| Glycerin | 3.2 |
| Polyvinyl alcohol[1] | 8.1 |
| Sodium Lauroamphoacetate (26% activity)[2] | 31.8 |
| Ammonium Laureth-3 sulfate (25% activity) | 4.9 |
| Ammonium Undecyl sulfate (24% activity) | 19.9 |
| Ammonium Laureth-1 sulfate (70% activity) | 8.0 |
| Cationic cellulose[3] | 0.5 |
| Citric Acid | 1.6 |
| Distilled water | 22.0 |
| | |
| Total | 100.0 |
| pH | 5.8 |
| Viscosity (cp) | 35,400 |

[1]Sigma-Aldrich Catalog No. 363081, MW 85,000-124,000, 87-89% hydrolyzed
[2]McIntyre Group Ltd, University Park, IL, Mackam HPL-28ULS
[3]UCARE ™ Polymer LR-400, available from Amerchol Corporation (Plaquemine, Louisiana)

A target weight of the above composition is prepared with the use of a conventional overhead stirrer (IKA® RW20DZM Stirrer available from IKA® Works, Inc., Wilmington, Del.) and a hot plate (Corning Incorporated Life Sciences, Lowell, Mass.). Into an appropriately sized and cleaned vessel, the distilled water and glycerin are added with stirring at 100-150 rpm. The cationic polymer, when present, is then slowly added with constant stirring until homogenous. The polyvinyl alcohol is weighed into a suitable container and slowly added to the main mixture in small increments using a spatula while continuing to stir while avoiding the formation of visible lumps. The mixing speed is adjusted to minimize foam formation. The mixture is slowly heated to 80° C. after which surfactants are added. The mixture is then heated to 85° C. while continuing to stir and then allowed to cool to room temperature. Additional distilled water is added to compensate for water lost to evaporation (based on the original tare weight of the container). The final pH is between 5.2-6.6 and adjusted with citric acid or diluted sodium hydroxide if necessary. The resulting processing mixture viscosity is measured.

Figure 4A:
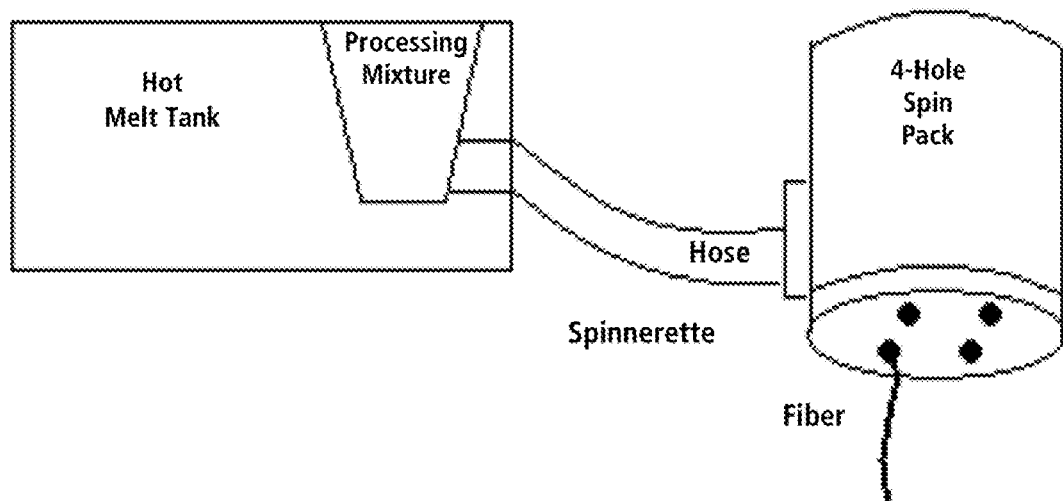
FIG. 4A is a diagram of setup for spinning processing mixture into fibers on a Four-Hole Spunbond Stand.
Figure 4B:
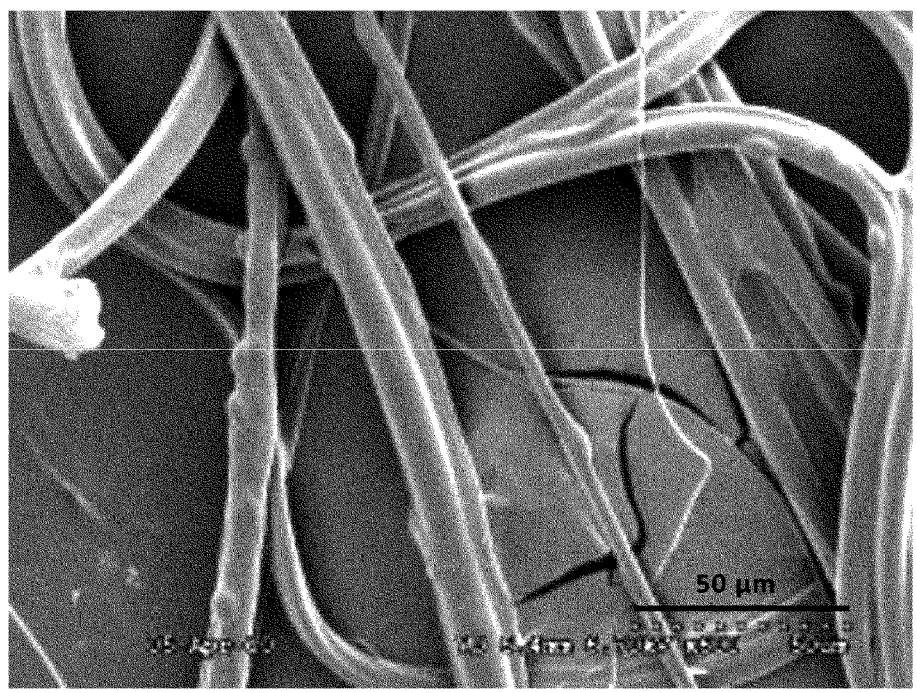
FIG. 4B is a SEM Photomicrograph of Spunbond Surfactant Containing Fibers.

The processing mixture was processed through a Four-Hole spunbond fiber spinning stand, which comprised a heated spin pack to the end of which was attached a spinnerette with four trilobal-shaped holes in it, three of which were plugged with graphite (See FIG. 4A). The processing mixture was heated to 200° F. in a hot melt tank and pumped through a hose into the Four-Hole spin pack, set to 207° F., by way of an adaptor plate (FIG. 4A). The processing mixture was then extruded out of the spin pack through the single open hole in the spinnerette. An air amplifier supplied with hot air was available as needed for use to simultaneously draw down and dry the extruded fiber. Mass throughput of the premix was controlled by the speed of the hot melt pump. Surfactant containing fibers were successfully made with widths ranging from 3-10 microns (FIG. 4B). Importantly, these fibers were demonstrated to dissolve within less than one second of coming into contact with water (FIG. 4C).

This example demonstrates the successful spinning of surfactant fibers from the above processing mixture composition employing a spunbond approach. The surfactant fibers were prepared from a processing mixture comprising 36% solids (35,400 cps) and the resulting solid fibers had the following estimated compositional parameters (assuming 0% moisture for ease of computation purposes—Note: Actual moisture level is expected to vary within 5% and 15% depending on the relative humidity in a laboratory setting):

| Solid Fibers Compositional Parameter | Estimated Value |
|---|---|
| Active Agent (Ionic Surfactants) | 60.6 wt. % |
| Water soluble polymeric structurant | 23.7 wt. % |
| Group I Surfactants (Anionic) | 36.3 wt. % |
| Group II Surfactants (Amphoteric) | 24.3 wt. % |
| Ratio of Group I:Group II | 60:40 |
| Ratio of Water soluble polymeric structurant to Active Agent | 0.39 |

Example 2: Preparation of Fibrous Dissolvable Solid Shampoo or Body Wash Article Via a Fluid Fibrillation Process The following processing composition is prepared at the indicated weight percentages as described in Table 2 below.

TABLE 2

| | |
|---|---|
| Glycerin | 13.5 |
| Polyvinyl alcohol[1] | 8.1 |
| Sodium Lauroamphoacetate (26% activity)[2] | 38.2 |
| Ammonium Laureth-3 sulfate (70% activity) | 2.9 |
| Ammonium Undecyl sulfate (70% activity) | 9.8 |
| Ammonium Laureth-1 sulfate (70% activity) | 9.8 |
| Cationic cellulose[3] | 0.5 |
| Citric Acid | 2.3 |
| Poly(ethylene oxide)[4] | 2.0 |
| Distilled water | 22.0 |
| | |
| Total | 100.0 |
| pH | 5.8 |
| Viscosity (cp) | 35,400 |

[1]Sigma-Aldrich Catalog No. 363081, MW 85,000-124,000, 87-89% hydrolyzed
[2]McIntyre Group Ltd, University Park, IL, Mackam HPL-28ULS
[3]UCARE ™ Polymer LR-400, available from Amerchol Corporation (Plaquemine, Louisiana)
[4]Average MW 8,000,000, available from Sigma Aldrich, Catalog Number 372838

A target weight of the above composition is prepared with the use of a conventional overhead stirrer (IKA® RW20DZM Stirrer available from IKA® Works, Inc., Wilmington, Del.) and a hot plate (Corning Incorporated Life Sciences, Lowell, Mass.). Into an appropriately sized and cleaned vessel, the distilled water and glycerin are added with stirring at 100-150 rpm. The cationic polymer and poly(ethylene oxide) is then slowly added with constant stirring until homogenous. The polyvinyl alcohol is weighed into a suitable container and slowly added to the main mixture in small increments using a spatula while continuing to stir while avoiding the formation of visible lumps. The mixing speed is adjusted to minimize foam formation. The mixture is slowly heated to 80° C. after which surfactants are added. The mixture is then heated to 85° C. while continuing to stir and then allowed to cool to room temperature. Additional distilled water is added to compensate for water lost to evaporation (based on the original tare weight of the container). The final pH is between 5.2-6.6 and adjusted with citric acid.

A hot melt tank was utilized to pump the heated processing mixture through a single orifice fluid film fibrillation nozzle system, holding constant the process parameters listed below:

| | |
|---|---|
| Tank set temperature | 200° F. |
| Hose set temperature | 200° F. |
| Nozzle set temperature | 250° F. |
| Mass flow | 2.7 g/min |

The air temperature, air pressure, and die-to-collector distance (DCD) were varied to assess their impact on spinning the processing mixture into fibers. The application of heated air produced significantly better results than ambient temperature air. Across an air temperature range from 89° F. to 400° F., fiber formation quality was best at 400° F. Higher air pressure (100 vs. 86 psi) was also found better for spinning. At a DCD of about 75 mm, air velocity at collection was high enough to splay the surfactant containing fibers, causing them to rope together into thick strings on the collection drum. When the DCD was increased to 130 mm, this effect was eliminated, and the laydown uniformity of surfactant fibers improved significantly.

Figure 3:
FIG. 3 SEM Photomicrograph (50×) of Melt Fibrillated Surfactant Containing Fibers.

This example demonstrates the successful spinning of surfactant fibers from the above processing mixture composition employing a fluid film fibrillation approach. An SEM image of the surfactant fibers is shown in FIG. 3. The surfactant fibers were prepared from a processing mixture comprising 52.1% solids and the resulting solid fibers had the following estimated compositional parameters (assuming 0% moisture for ease of computation purposes—Note: Actual moisture level is expected to vary within 5% and 15% depending on the relative humidity in a laboratory setting):

| Solid Fibers Compositional Parameter | Estimated Value |
|---|---|
| Active Agent (Ionic Surfactants) | 49.4 wt. % |
| Water soluble polymeric structurant | 15.5 wt. % |
| Extensional Rheology Modifier - polyethylene oxide (weight-average molecular weight = 8,000,000 Daltons) | 3.8 wt. % |
| Group I Surfactants (Anionic) | 30.3 wt. % |
| Group II Surfactants (Amphoteric) | 19.1 wt. % |
| Ratio of Group I:Group II | 61.3:38.7 |
| Ratio of Water soluble polymeric structurant to Active Agent | 0.31 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition comprising:
   (a) at least one layer of a nonwoven fibrous web structure comprising a water soluble polymer, and
   (b) sugar alcohol,
   wherein the oral care composition is an oral care article.

2. The oral care composition of claim 1, wherein the composition further comprises a first surfactant.

3. The oral care composition of claim 1, wherein the composition further comprises an active agent.

4. The oral care composition of claim 2, wherein the composition further comprises a second surfactant.

5. The oral care composition of claim 1, wherein the oral care article is a teeth cleaning article, teeth whitening article, tooth care article, periodontal gum care article, denture cleaning article, tongue cleaning article, breath freshening article, fluoride containing article, mouth rinse article, anti-cavity article, or a combination thereof.

6. The oral care composition of claim 1, wherein the water soluble polymer comprises a polyvinyl alcohol, polyacrylate, polymethacrylate, copolymer of acrylic acid and methyl acrylate, polyvinylpyrrolidone, polyalkylene oxide, starch, starch derivative, pullulan, gelatin, hydroxypropylmethylcellulose, methycellulose, carboxymethycellulose, or a combination thereof.

7. The oral care composition of claim 2, wherein the first surfactant comprises an anionic surfactant, a zwitterionic surfactant, or a combination thereof.

8. The oral care composition of claim 2, wherein the first surfactant comprises an alkyl sulfate, alkyl ether sulfate, sulfated monoglyceride, sulfonated olefin, alkyl aryl sulfonate, primary, alkane sulfonate, secondary alkane sulfonate, alkyl sulfosuccinate, acid taurate, acid isethionate, alkyl glycerylether sulfonate, sulfonated methyl ester, sulfonated fatty acid, alkyl phosphate, acyl glutamate, acyl sarcosinate, alkyl lactylate, anionic fluorosurfactant, sodium lauroyl glutamate, or a combination thereof.

9. The oral care composition of claim 2, wherein the first surfactant comprises a sodium laureth sulfate.

10. The oral care composition of claim 2, wherein the first surfactant comprises a betaine.

11. The oral care composition of claim 2, wherein the sugar alcohol comprises a polyhydric alcohol with from two to eight carbon atoms.

12. The oral care composition of claim 4, wherein the second surfactant comprises an amphoteric surfactant, a nonionic surfactant, a cationic surfactant, a zwitterionic surfactant, or a combination thereof.

13. The oral care composition of claim 12, wherein the nonionic surfactant comprises polyethylene glycol.

14. The oral care composition of claim 12, wherein the zwitterionic surfactant comprises betaine.

15. The oral care composition of claim 12, wherein the cationic surfactant comprises quaternary ammonium salt.

16. The oral care composition of claim 12, wherein the cationic surfactant comprises cetylpyridinium chloride.

17. The oral care composition of claim 1, wherein the oral care article comprises a liquid composition and at least two layers of a nonwoven fibrous web structure.

18. The oral care composition of claim 17, wherein at least a portion of the liquid composition is between the at least two layers of a nonwoven fibrous web structure.

19. The oral care composition of claim 17, wherein the liquid composition is water-releasable.

20. The oral care composition of claim 1, wherein the oral care composition comprises a high surface area particle.

21. The oral care composition of claim 20, wherein the high surface area particle comprises an amorphous silica, amorphous silica gel, precipitated silica, fumed silica, alumina, silicate, carbonate, or a combination thereof.

22. An oral care article comprising:
(a) at least one layer of a nonwoven fibrous web structure comprising a water soluble polymer,
(b) a first surfactant comprising anionic surfactant, a zwitterionic surfactant, or a combination thereof, and
(c) a second surfactant.

23. The oral care article of claim 22, wherein the first surfactant comprises an alkyl sulfate, alkyl ether sulfate, sulfated monoglyceride, sulfonated olefin, alkyl aryl sulfonate, primary, alkane sulfonate, secondary alkane sulfonate, alkyl sulfosuccinate, acid taurate, acid isethionate, alkyl glycerylether sulfonate, sulfonated methyl ester, sulfonated fatty acid, alkyl phosphate, acyl glutamate, acyl sarcosinate, alkyl lactylate, anionic fluorosurfactant, sodium lauroyl glutamate, or a combination thereof.

24. The oral care article of claim 22, wherein the first surfactant comprises alkyl sulfate, betaine, or combinations thereof.

25. The oral care article of claim 22, wherein the second surfactant comprises an amphoteric surfactant, a nonionic surfactant, a cationic surfactant, a zwitterionic surfactant, or a combination thereof.

26. The oral care article of claim 22, wherein the second surfactant comprises polyethylene glycol, cetyl pyridinium chloride, or combinations thereof.

27. An oral article comprising:
(a) at least one layer of a nonwoven fibrous web structure comprising a water soluble polymer, and
(b) sugar alcohol.

28. The oral care article of claim 27, wherein the sugar alcohol comprises a polyhydric alcohol with from two to eight carbon atoms.

* * * * *